US011859239B2

(12) United States Patent
Kawashima et al.

(10) Patent No.: US 11,859,239 B2
(45) Date of Patent: Jan. 2, 2024

(54) NUCLEIC ACID SAMPLE-CONTAINED CONTAINER, METHOD AND APPARATUS FOR PRODUCING NUCLEIC ACID SAMPLE-CONTAINED CONTAINER, NON-TRANSITORY RECORDING MEDIUM STORING PROGRAM FOR PRODUCING NUCLEIC ACID SAMPLE-CONTAINED CONTAINER, AND NUCLEIC ACID SAMPLE

(71) Applicant: RICOH COMPANY, LTD., Tokyo (JP)

(72) Inventors: Yudai Kawashima, Kanagawa (JP); Masayuki Yumoto, Kanagawa (JP); Satoshi Izumi, Tokyo (JP); Manabu Seo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/356,591

(22) Filed: Mar. 18, 2019

(65) Prior Publication Data
US 2019/0284611 A1   Sep. 19, 2019

(30) Foreign Application Priority Data

Mar. 19, 2018 (JP) ................. 2018-051756
Mar. 19, 2018 (JP) ................. 2018-051757
Mar. 11, 2019 (JP) ................. 2019-043914

(51) Int. Cl.
*C12Q 1/6806* (2018.01)
*C12Q 1/6809* (2018.01)
(Continued)

(52) U.S. Cl.
CPC ............. *C12Q 1/6806* (2013.01); *B01L 3/56* (2013.01); *B01L 7/52* (2013.01); *B41M 5/0023* (2013.01);
(Continued)

(58) Field of Classification Search
CPC ............ C12Q 1/6851; C12Q 2545/113; C12Q 1/6809; C12Q 2537/16; C12Q 2563/159;
(Continued)

(56) References Cited

U.S. PATENT DOCUMENTS

2005/0032192 A1   2/2005   Vesey et al.
2005/0037397 A1 *  2/2005   Mirkin .................. B82Y 30/00
                                                                  506/4
(Continued)

FOREIGN PATENT DOCUMENTS

JP           3744766 B2     12/2005
JP           2008245612     10/2008
(Continued)

OTHER PUBLICATIONS

Extended European Search Report dated Jun. 14, 2019 in European Patent Application No. 19162995.5, 7 pages.
(Continued)

*Primary Examiner* — Joseph G. Dauner
(74) *Attorney, Agent, or Firm* — Grüneberg and Myers, PLLC

(57) ABSTRACT

Provided is a nucleic acid sample-contained container including: a first nucleic acid molecule including an intended base sequence and a base sequence for detection different from the intended base sequence; and a second nucleic acid molecule free of the intended base sequence but including the base sequence for detection, wherein the nucleic acid sample-contained container includes the first nucleic acid molecule in a predetermined number. In a preferable mode, the copy number of the intended base sequence is less than 1,000, and the coefficient of variation (CV value) for the copy number is lower than 20%. In a more preferable mode, the nucleic acid molecules are artificially synthesized nucleic acid molecules. In a yet more
(Continued)

preferable mode, the first nucleic acid molecule includes the intended base sequence in a plural number in the same molecule.

15 Claims, 16 Drawing Sheets

Specification includes a Sequence Listing.

(51) Int. Cl.

| | | |
|---|---|---|
| C12Q 1/68 | (2018.01) | |
| B01L 3/00 | (2006.01) | |
| B01L 7/00 | (2006.01) | |
| B41M 5/00 | (2006.01) | |
| G01N 21/64 | (2006.01) | |

(52) U.S. Cl.
CPC ............ *C12Q 1/68* (2013.01); *C12Q 1/6809* (2013.01); *G01N 21/6428* (2013.01); *G01N 2021/6439* (2013.01)

(58) Field of Classification Search
CPC .. C12Q 1/68; C12Q 2563/179; C12Q 1/6806; G01N 2021/6439; G01N 21/6428; B01J 2219/00547; B01J 2219/00317; B01L 3/56; B01L 7/52; B01L 2200/0652; B01L 3/508; B41M 5/0023
See application file for complete search history.

(56) References Cited

U.S. PATENT DOCUMENTS

| | | | |
|---|---|---|---|
| 2008/0003142 A1 | 1/2008 | Link et al. | |
| 2008/0014589 A1 | 1/2008 | Link et al. | |
| 2008/0241841 A1 | 10/2008 | Murakawa et al. | |
| 2011/0294139 A1 | 12/2011 | Takeda | |
| 2012/0164633 A1 | 6/2012 | Laffler | |
| 2012/0288920 A1 | 11/2012 | Takeda | |
| 2013/0090248 A1 | 4/2013 | Link et al. | |
| 2013/0183659 A1 | 7/2013 | Link et al. | |
| 2013/0210639 A1 | 8/2013 | Link et al. | |
| 2014/0378345 A1* | 12/2014 | Hindson | C12Q 1/6806 506/16 |
| 2015/0133319 A1 | 5/2015 | Fu et al. | |
| 2016/0312276 A1* | 10/2016 | Fu | C12Q 1/6855 |
| 2016/0324934 A1 | 11/2016 | Angel et al. | |
| 2017/0304785 A1 | 10/2017 | Link et al. | |
| 2017/0307502 A1* | 10/2017 | Mason | B01L 3/0241 |
| 2017/0307626 A1 | 10/2017 | Griffiths et al. | |
| 2018/0178174 A1 | 6/2018 | Link et al. | |
| 2018/0272295 A1 | 9/2018 | Link et al. | |
| 2018/0272296 A1 | 9/2018 | Link et al. | |
| 2018/0280897 A1 | 10/2018 | Link et al. | |

FOREIGN PATENT DOCUMENTS

| | | |
|---|---|---|
| JP | 4414220 | 2/2010 |
| JP | 5229895 B2 | 3/2013 |
| JP | 2013-521764 | 6/2013 |
| JP | 5382852 | 1/2014 |
| JP | 2014-033658 A | 2/2014 |
| JP | 2015511819 | 4/2015 |
| JP | 2015-195735 A | 11/2015 |
| JP | 2015-198652 A | 11/2015 |
| JP | 6031178 | 11/2016 |
| JP | 2016-217887 A | 12/2016 |
| JP | 2017510542 | 4/2017 |
| JP | 2017-532560 | 11/2017 |
| JP | 2019-024453 A | 2/2019 |
| WO | WO 2007/133710 A2 | 11/2007 |

OTHER PUBLICATIONS

Samuel C Kim et al, "Measurement of copy number variation in single cancer cells using rapid-emulsification digital droplet MDA", Microsystems & Nanoengineering (2017) 3, 17018; doi:10.1038/micronano.2017.18.

Linas Mazutis et al, "Single-cell analysis and sorting using droplet-based microfluidics", Nat Protoc. May 2013 ; 8(5):870-891, doi:10.1038/nprot.2013.046.

U.S. Appl. No. 16/196,790, filed Nov. 20, 2018 (unpublished application, specification included).

Japanese Office Action dated Nov. 8, 2022, in Japanese Application No. 2019-043914, 4 pages.

* cited by examiner

NUCLEIC ACID SAMPLE-CONTAINED CONTAINER, METHOD AND APPARATUS FOR PRODUCING NUCLEIC ACID SAMPLE-CONTAINED CONTAINER, NON-TRANSITORY RECORDING MEDIUM STORING PROGRAM FOR PRODUCING NUCLEIC ACID SAMPLE-CONTAINED CONTAINER, AND NUCLEIC ACID SAMPLE

CROSS-REFERENCE TO RELATED APPLICATIONS

The present application claims priority under 35 U.S.C. § 119 to Japanese Patent Application No. 2018-051757 filed Mar. 19, 2018, Japanese Patent Application No. 2018-051756 filed Mar. 19, 2018, and Japanese Patent Application No. 2019-043914 filed Mar. 11, 2019. The contents of which are incorporated herein by reference in their entirety.

BACKGROUND OF THE INVENTION

Field of the Invention

The present disclosure relates to a nucleic acid sample-contained container, a method and an apparatus for producing a nucleic acid sample-contained container, a non-transitory recording medium storing a program for producing a nucleic acid sample-contained container, and a nucleic acid sample.

Description of the Related Art

Nucleic acid analyzing techniques are widely used in various fields such as food inspection, blood tests, and DNA (deoxyribonucleic acid) tests. Representative examples of the nucleic acid analyzing techniques include real-time polymerase chain reaction (PCR) methods.

Real-time PCR is a method for quantifying the amount of nucleic acid in an analyte by timely detecting fluorescence corresponding to amplification of nucleic acid in a PCR process and relatively comparing serial standard samples having prescribed copy numbers with the number of nucleic acid detected in the intended analyte.

However, in quantification of nucleic acid in an analyte, there is a need for abstracting only the nucleic acid from PCR reaction inhibitors such as blood corpuscles, sugars, and fats in the analyte. Further, when the intended nucleic acid is RNA, there is a need for reverse transcription to cDNA. Hence, in order to quantify nucleic acid in the analyte, there is a need for taking into account the efficiency for extracting nucleic acid molecules, such as the nucleic acid abstraction efficiency and the reverse transcription efficiency.

Hence, in order to take into account the efficiency for extracting nucleic acid, it is common to carry out a method of performing abstraction, reverse transcription, and real-time PCR with addition of, for example, a standard nucleic acid sample having a prescribed concentration in the reaction system as an internal standard, and quantifying the initial nucleic acid amount and the efficiency in each step.

Hitherto, in order to produce a standard reagent for a low nucleic acid concentration range among nucleic acid standard samples used as internal standards, there has been proposed a method for diluting DNA fragments having a specific base sequence by a limiting dilution method and selecting a diluted solution containing the intended number of copies based on the result of quantitative PCR of the obtained diluted solutions (for example, see Japanese Unexamined Patent Application Publication No. 2014-33658).

There has also been proposed a method of introducing a specific copy number of DNA fragments into cells by a gene recombination technique, and manually isolating the cells into which the DNA fragments have been introduced, to produce a standard reagent containing the intended copy number of DNA fragments (for example, see Japanese Unexamined Patent Application Publication No. 2015-195735).

There has also been proposed a method of amplifying an intended base sequence region of a nucleic acid within droplets or gel droplets, and sorting (separating) droplets or gel droplets in which a nucleic acid amplification reaction has occurred (for example, see Japanese Unexamined Patent Application Publication No. 2008-245612).

SUMMARY OF THE INVENTION

According to one aspect of the present disclosure, a nucleic acid sample-contained container includes a first nucleic acid molecule including an intended base sequence and a base sequence for detection different from the intended base sequence, and a second nucleic acid molecule free of the intended base sequence but including the base sequence for detection. The nucleic acid sample-contained container includes the first nucleic acid molecule in a predetermined number.

Figure 1:
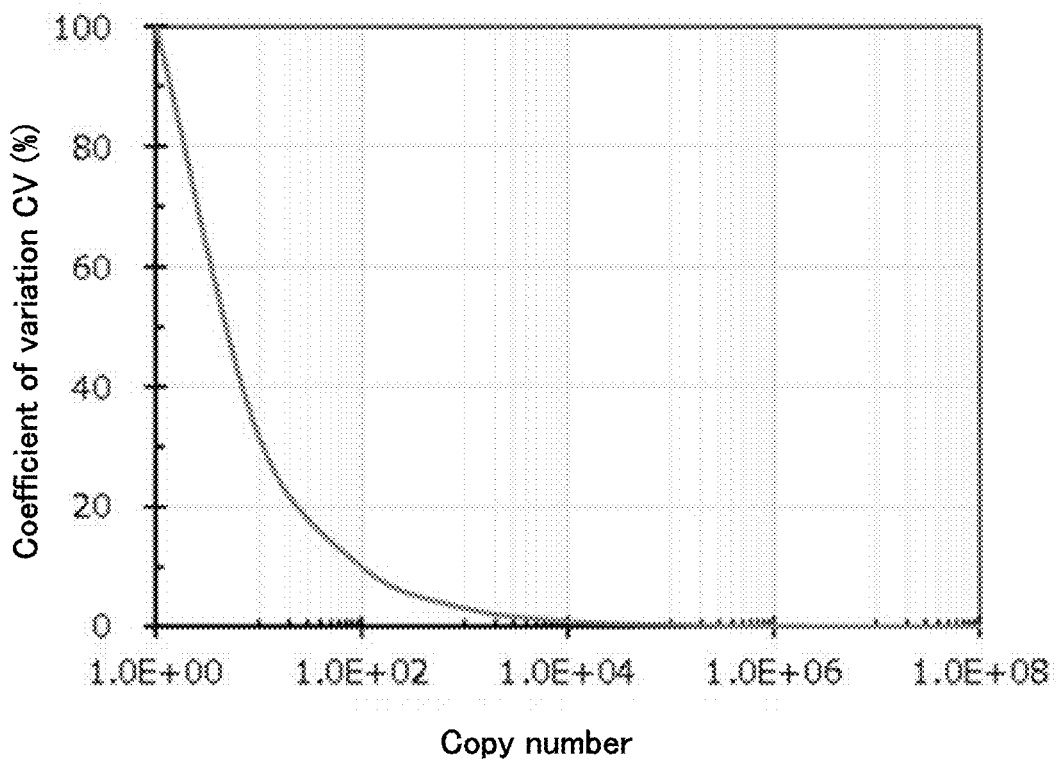
FIG. 1 is a graph plotting a relationship between a copy number and a coefficient of variation CV.

DESCRIPTION OF THE EMBODIMENTS (Nucleic Acid Sample-Contained Container)

A nucleic acid sample-contained container of the present disclosure includes a first nucleic acid molecule including an intended base sequence and a base sequence for detection different from the intended base sequence, and a second nucleic acid molecule free of the intended base sequence but including the base sequence for detection. The nucleic acid sample-contained container includes the first nucleic acid molecule in a predetermined number. The nucleic acid sample-contained container further includes a solution and, as needed, other materials.

The present disclosure has an object to provide a nucleic acid sample-contained container in which a nucleic acid including an intended base sequence in a predetermined number is contained in a desired number of molecules (in a known copy number).

The present disclosure can provide a nucleic acid sample-contained container in which a nucleic acid including an intended base sequence in a predetermined number is contained in a desired number of molecules (in a known copy number).

The present inventors have achieved the following findings as a result of studying a nucleic acid sample-contained container in which a nucleic acid including an intended base sequence in a predetermined number is contained in a desired number of molecules (in a known copy number).

There is a problem with the standard nucleic acid sample used in the above-described quantification method using real-time PCR. Namely, as presented by the related art, in the case of selecting a diluted solution containing a specific number of molecules (copies) based on the result of real-time PCR of diluted solutions of nucleic acid including the intended based sequence, dilution of less than a hundred nucleic acid molecules (copies) results in a high uncertainty of the number of nucleic acid molecules (copies) to be contained in the diluted solutions under influence of a Poisson distribution, indicating a difficulty producing a standard reagent containing an arbitrary number of nucleic acid molecules.

According to the method of the related art employing a gene recombination technique, because bothersome operations such as gene recombination and cell culture are needed before cells into which an intended based sequence has been introduced by the gene recombination technique are ready for use, there is a problem of difficulty producing a standard nucleic acid sample in a short time. Moreover, because a standard nucleic acid sample, which is produced by introducing a nucleic acid including an intended base sequence into cells and processing isolated cells, contains contaminants attributable to the cells (for example, proteins and lipids), there is a problem of a possibility of contaminating the reaction system.

Furthermore, the related art describes a method of independently amplifying a plurality of kinds of nucleic acids by minute segmentation and sorting (separating) minute segments (droplets or gel droplets) in which a nucleic acid amplification reaction has occurred. Because a plurality of kinds of nucleic acids are contained in the minute segments, there is a problem of difficulty ensuring the presence of only one kind of nucleic acid molecules in a minute segment that is detected as positive, making it difficult to obtain a nucleic acid sample including the intended base sequence in the desired number of molecules (also referred to as a copy number that is a predetermined number or as a specific copy number).

Furthermore, because the standard nucleic acid samples produced according to the related art are present in the state of a solution or a suspension, there is a problem of difficulty for the user to add the standard nucleic acid samples in needed amounts in an arbitrary reaction system.

By including the first nucleic acid molecule in the predetermined number, the nucleic acid sample-contained container of the present disclosure is excellent in storage stability of the first nucleic acid molecule serving as a nucleic acid sample and in user's handleability. Moreover, because the number of nucleic acid molecules (the copy (unit) number of the intended base sequence) contained in the nucleic acid sample-contained container is known, it is possible to add the nucleic acid sample in a trace needed amount in an arbitrary reaction system. Here, the trace amount refers to a number of molecules of about 1 molecule or greater but 1,000 molecules or less.

In the present disclosure, a predetermined base sequence may be referred to as "copy" to serve as a basic unit, and there may be a case where the number of the predetermined base sequence is counted as a unit (for example, one intended base sequence is counted as one copy). Further, one continuous nucleic acid including this predetermined base sequence and another base sequence may be, as one unit, referred to as one molecule, for example.

A copy number means the number of target or specific base sequences (the number of sense strands) in a nucleic acid contained in a well.

The target base sequence refers to a base sequence including defined base sequences in at least primer and probe regions. Specifically, a base sequence having a defined total length is also referred to as specific base sequence.

A specific copy number refers to the aforementioned copy number that specifies the number of target base sequences at accuracy of a certain level or higher.

This means that the specific copy number is a known number as the number of target base sequences actually contained in a container (examples of the container including a particle and a well). That is, the specific copy number in the present disclosure is more accurate or reliable as a number than a copy number (calculated estimated value) obtained according to existing serial dilution methods, and is a controlled value that has no dependency on a Poisson distribution even if the value is within a low copy number region of 1,000 or lower in particular. When it is said that the specific copy number is a controlled value, it is preferable that a coefficient of variation CV expressing uncertainty roughly satisfy either $CV<1/\sqrt{x}$ with respect to an average copy number x or $CV \leq 20\%$. Hence, use of a container (examples of the container including a particle and a well) in which a target base sequence is contained in the specific copy number makes it possible to perform qualitative or quantitative testing of samples containing the target base sequence more accurately than ever.

In the case of a nucleic acid molecule such as double-strand DNA in which a target base sequence (sense strand) and a complementary strand (antisense strand) having a complementary base sequence are integrated, instead of counting the number of target base sequences in the sense strand as the copy number, there is a need for considering the total copy number summing "the number of target base sequences in the sense strand" and "the number of strands complementary with the target base sequence and included in the antisense strand" to be "the copy number" of the target base sequence present in the reaction system.

In the present disclosure, a specific copy number of the nucleic acid may be referred to as predetermined number or absolute number of the nucleic acid.

The specific copy number of the nucleic acid is preferably 1 copy or greater but 1,000 copies or less, preferably 100 copies or less, more preferably 20 copies or less, and yet more preferably 10 copies or less.

—Nucleic Acid—

A nucleic acid means a polymeric organic compound in which a nitrogen-containing base derived from purine or pyrimidine, sugar, and phosphoric acid are bonded with one another regularly. Examples of the nucleic acid also include a fragment of a nucleic acid or an analog of a nucleic acid or of a fragment of a nucleic acid.

The nucleic acid is not particularly limited and may be appropriately selected depending on the intended purpose. Examples of the nucleic acid include DNA, RNA, and cDNA. As the nucleic acid, a plasmid can also be used. The nucleic acid may be modified or mutated.

Examples of the analog of a nucleic acid or a nucleic acid fragment include a nucleic acid or a nucleic acid fragment bonded with a non-nucleic acid component, a nucleic acid or a nucleic acid fragment labeled with a labeling agent such as a fluorescent dye or an isotope (e.g., a primer or a probe labeled with a fluorescent labeling dye or a radioisotope), and an artificial nucleic acid, which is a nucleic acid or a nucleic acid fragment in which the chemical structure of some of the constituent nucleotides is changed (e.g., PNA, BNA, and LNA).

When one nucleic acid molecule includes the intended base sequence described below in a plural number, it is preferable that the one nucleic acid molecule include at least one artificial nucleic acid base unamplifiable by a natural nucleic acid synthetase (e.g., DNA polymerase) between the individual intended base sequences. With at least one artificial nucleic acid base unamplifiable by a natural nucleic acid synthetase (e.g., DNA polymerase) included between the individual intended base sequences, even when one molecule includes the intended base sequence in a plural number, each copy of the intended base sequence is amplified independently. Therefore, a plurality of amplification products can be obtained at a time even when the number of nucleic acid molecules including the intended base sequence is low.

The artificial nucleic acid may be a natural product obtained from a living thing, or a processed product of the natural product, or a product produced by utilizing a genetic recombination technique, or a chemically synthesized artificially synthesized nucleic acid molecule. One of these artificial nucleic acids may be used alone or two or more of these artificial nucleic acids may be used in combination. With an artificially synthesized nucleic acid molecule, it is possible to suppress impurities and reduce the molecular weight. This makes it possible to improve the initial reaction efficiency.

An artificially synthesized nucleic acid molecule means an artificially synthesized nucleic acid produced to have the same constituent components (base, deoxyribose, and phosphoric acid) as naturally existent DNA or RNA. Examples of the artificially synthesized nucleic acid molecule include not only a nucleic acid having a base sequence coding a protein, but also a nucleic acid having an arbitrary base sequence.

——First Nucleic Acid Molecule——

A first nucleic acid molecule includes an intended base sequence and a base sequence for detection different from the intended base sequence.

The nucleic acid sample-contained container of the present disclosure includes the first nucleic acid molecule in a predetermined number.

The predetermined number of the first nucleic acid molecule is not particularly limited, may be appropriately selected depending on the intended purpose, and is preferably 100 molecules or less.

The form of the first nucleic acid molecule is not particularly limited and may be appropriately selected depending on the intended purpose. Examples of the form of the first nucleic acid molecule include double-strand nucleic acid molecule (dsDNA or dsRNA) and single-strand nucleic acid molecule (ssDNA or ssRNA), and nucleic acid molecule in which double-strand nucleic acid molecules and single-strand nucleic acid molecules are intermixed. A nucleic acid molecule in which double-strand nucleic acid molecules and single-strand nucleic acid molecules are intermixed refers to a nucleic acid molecule, which is the first nucleic acid molecule in which double-strand portions and single-strand portions are intermixed.

——Intended Base Sequence——

The intended base sequence is not particularly limited and may be appropriately selected, so long as the intended base sequence is a base sequence different from the base sequence for detection described below. The intended base sequence may hereinafter be referred to as base sequence different from the base sequence for detection (or different sequence). Examples of the intended base sequence include the followings.

Examples of the intended base sequence include base sequences used for infectious disease testing, naturally non-existent non-natural base sequences, animal cell-derived base sequences, and plant cell-derived base sequences. One of these intended base sequences may be used alone or two or more of these intended base sequences may be used in combination.

In the case of using a non-natural base sequence, the intended base sequence preferably has a GC content of 30% or higher but 70% or lower.

The base length of the intended base sequence is not particularly limited, may be appropriately selected depending on the intended purpose, and may be, for example, a base length of 20 base pairs (or mer) or longer but 10,000 base pairs (or mer) or shorter.

The form of the intended base sequence is not particularly limited and may be appropriately selected depending on the intended purpose. Examples of the form of the intended base sequence include double-strand nucleic acid (dsDNA or dsRNA), single-strand nucleic acid (ssDNA or ssRNA), and nucleic acid in which double-strand nucleic acid molecules and single-strand nucleic acid molecules are intermixed. Among these forms, the intended base sequence is preferably a single-strand nucleic acid. When the intended base sequence is a single-strand nucleic acid, what are to be used can be only sense strands having the intended base sequence. This enables a more highly accurate control on the copy number of the intended base sequence in the nucleic acid sample-contained container than in the case of using double-strand nucleic acid also including an antisense strand.

In the case of using a base sequence used for infectious disease testing, the intended base sequence is not particularly limited and may be appropriately selected depending on the intended purpose so long as the intended base sequence includes a base sequence specific to the intended infectious disease. It is preferable that the intended base sequence include a base sequence designated in official analytical methods or officially announced methods.

The intended base sequence included in the nucleic acid sample-contained container of the present disclosure may be arbitrarily selected depending on the purpose intended by the user. For example, the intended base sequence is preferably a base sequence used in a publicly known standard nucleic acid sample. When a base sequence used in a publicly known standard nucleic acid sample is selected as the intended base sequence, the intended base sequence can be used as an internal standard for real-time PCR.

———Base Sequence for Detection———

The base sequence for detection is a base sequence different from the intended base sequence described above, and is a base sequence used for confirming presence or absence of a nucleic acid including the intended base sequence. The base sequence for detection needs at least be a base sequence whose at least primer region and probe region are known at the time of working of the present disclosure, and is a base sequence that is amplified under a condition under which the intended base sequence is not amplified.

The base sequence for detection is not particularly limited and may be appropriately selected depending on the intended purpose, so long as the base sequence for detection is a base sequence different from the intended base sequence.

The base sequence for detection preferably has a GC content of 30% or higher but 70% or lower because the base sequence for detection is amplified by an amplifying unit described below.

The base length of the base sequence for detection is not particularly limited, may be appropriately selected depending on the intended purpose, and is preferably, for example, a base length of 20 base pairs (or mer) or longer but 1,000 base pairs (or mer) or shorter.

The copy (unit) number of the base sequence for detection is not particularly limited and may be appropriately selected depending on the intended purpose.

The form of the base sequence for detection is not particularly limited and may be appropriately selected depending on the intended purpose. Examples of the form of the base sequence for detection include double-strand nucleic acid (dsDNA or dsRNA), single-strand nucleic acid (ssDNA or ssRNA), and nucleic acid in which double-strand nucleic acid molecules and single-strand nucleic acid molecules are intermixed. Among these forms, the base sequence for detection is preferably a single-strand nucleic acid (ssDNA or ssRNA). When the base sequence for detection is a single-strand nucleic acid, the first nucleic acid molecule can be detected without a change in the copy number of the intended base sequence in a method of the present disclosure for producing a nucleic acid sample-contained container described below. This makes it possible to improve the accuracy of the copy number of the intended base sequence to be contained in the nucleic acid sample-contained container of the present disclosure. When it is said that the base sequence for detection is a single-strand nucleic acid, it is meant that at least the base sequence for detection in the first nucleic acid molecule is a single-strand nucleic acid.

The position of the base sequence for detection in the first nucleic acid molecule is not particularly limited and may be appropriately selected.

When the base sequence for detection is a single-strand nucleic acid molecule and present at the 5' terminal side of the intended base sequence, the intended base sequence can be detected without a change in the copy number of the intended base sequence in the first nucleic acid molecule in a method of the present disclosure for producing a nucleic acid sample-contained container described below. This makes it possible to improve the accuracy of the copy number of the intended base sequence to be contained in the nucleic acid sample-contained container of the present disclosure. A synergetic effect obtained from this configuration can better improve the accuracy of the copy number of the intended base sequence to be contained in the nucleic acid sample-contained container of the present disclosure.

The distance between the intended base sequence and the base sequence for detection is not particularly limited and may be appropriately selected depending on the intended purpose so long as the intended base sequence and the base sequence for detection is apart from each other sufficiently. For example, it is preferable that the intended base sequence and the base sequence of detection be apart by longer than or equal to 500 base pairs (or mer). However, this is not the case when the base sequence for detection is a single-strand nucleic acid and present at the 5' terminal side of the intended base sequence. When the intended base sequence and the base sequence for detection is apart from each other sufficiently, the intended base sequence can be detected without a change in the copy number of the intended base sequence in the first nucleic acid molecule in a method of the present disclosure for producing a nucleic acid sample-contained container described below. This makes it possible to improve the accuracy of the copy number of the intended base sequence to be contained in the nucleic acid sample-contained container of the present disclosure.

——Second Nucleic Acid Molecule——

The second nucleic acid molecule is a nucleic acid molecule free of the intended base sequence described above but including the base sequence for detection.

The base sequence for detection in the second nucleic acid molecule is a base sequence amplified on a template, which is the base sequence for detection included in the first nucleic acid molecule in the production of the nucleic acid sample-contained container of the present disclosure.

It is preferable that the nucleic acid in the nucleic acid sample-contained container of the present disclosure be in a dry state or in a state of being dispersed in a solution. When the nucleic acid is in a dry state, it is possible to reduce the possibility of the nucleic acid being degraded by an enzyme, and it is possible to store the nucleic acid at normal temperature.

<Solution>

The solution is not particularly limited and may be appropriately selected depending on the intended purpose, so long as the nucleic acid can be dispersed in the solution without being influenced by the solution. Examples of the solution include water, nuclease-free water, a broth, a separation liquid, a diluted solution, a buffer, an organic substance lysing liquid, an organic solvent, a polymer gel solution, a colloid dispersion liquid, an electrolyte aqueous solution, an inorganic salt aqueous solution, a metal aqueous solution, and a mixture liquid of these solutions. Among these solutions, water and a buffer are preferable, and water, nuclease-free water, a phosphate buffered saline (PBS), and a Tris-EDTA buffer (TE) are preferable. One of these solutions may be used alone or two or more of these solutions may be used in combination.

For example, a nucleic acid amplifying reagent used in the method of the present disclosure for producing a nucleic acid sample-contained container described below may remain in the solution. Description about, for example, the nucleic acid amplifying reagent is skipped here, because, for example, the nucleic acid amplifying reagent will be described in detail in the method of the present disclosure for producing a nucleic acid sample-contained container described below.

The first nucleic acid and the second nucleic acid in the nucleic acid sample-contained container of the present disclosure may be in a state of being encapsulated in a dispersed phase or in a state of being carried on a dispersed phase.

<Dispersed Phase>

A dispersed phase means a segment defined to have a minute size. The dispersed phase is not particularly limited and may be appropriately selected depending on the intended purpose. Examples of the dispersed phase include a liquid dispersed phase and a solid dispersed phase.

Examples of the liquid dispersed phase include a water-in-oil droplet (W/O type) or an oil-in-water droplet (O/W type) forming a water-oil-based emulsion, and a micelle. The volume of the dispersed phase can be controlled based on, for example, a flow rate of a continuous phase, a flow rate of a dispersed phase, a flow path width, a flow path height, a surfactant concentration, a solution viscosity, and pressure loss of a flow path in the preparation of dispersed phases in the method of the present disclosure for producing a nucleic acid sample-contained container described below. The volume of the dispersed phase is preferably 1 fL or greater but 1 microliter or less.

Examples of the solid dispersed phase include a nucleic acid that is captured in unit of one molecule onto a particle that can capture a nucleic acid from a nucleic acid-containing liquid.

The particle is not particularly limited and may be appropriately selected depending on the intended purpose. Examples of the particle include a particle modified on the surface with a nucleic acid probe specifically bindable with a nucleic acid including the intended base sequence, and a silica particle to which a nucleic acid is adsorbed by a solid phase adsorption method in the presence of a chaotropic substance.

The particle modified on the surface with a nucleic acid probe specifically bindable with a nucleic acid including the intended base sequence is not particularly limited and may be appropriately selected depending on the intended purpose, so long as the particle is modified on the surface with a nucleic acid probe specifically bindable with a nucleic acid including the intended base sequence. Examples of the particle modified on the surface with a nucleic acid probe specifically bindable with a nucleic acid including the intended base sequence include: metals such as gold, silver, copper, aluminum, tungsten, molybdenum, chromium, platinum, titanium, and nickel; alloys such as stainless steel, hastelloy, Inconel, monel, and duralumin; silicon; glass materials such as glass, quartz glass, fused quartz, synthetic quartz, alumina, sapphire, ceramics, forsterite, and photosensitive glass; plastics such as polyester resins, polystyrene, polyethylene resins, polypropylene resins, ABS resins (Acrylonitrile Butadiene Styrene resins), nylon, acrylic resins, fluororesins, polycarbonate resins, polyurethane resins, methylpentene resins, phenol resins, melamine resins, epoxy resins, and vinyl chloride resins; and agarose, dextran, cellulose, polyvinyl alcohol, nitrocellulose, chitin, and chitosan. One of these particles may be used alone or two or more of these particles may be used in combination. Moreover, a magnetic bead that is magnetized, or encapsulates a magnetic body, or is magnetizable may be used as the particle. This makes it possible to automate, streamline, or expedite, for example, a separation operation.

The number of the particles modified on the surface with a nucleic acid probe specifically bindable with a nucleic acid including the intended base sequence is preferably, a number that is at a ratio at which the number of nucleic acid including the intended base sequence per particle is one molecule or less. For example, it is preferable to adjust the number of particles to about 1 time or more but 10 times or less greater than the number of nucleic acid including the intended base sequence.

The method for modifying the surface of the particle with a nucleic acid probe specifically bindable with a nucleic acid including the intended base sequence is not particularly limited and may be appropriately limited depending on the intended purpose. Examples of the method include immobilization methods using covalent bond, ionic bond, physical adsorption, or biological binding (for example, binding with biotin, avidin, or streptavidin, and antigen-antibody binding).

The nucleic acid probe specifically bindable with a nucleic acid including the intended base sequence may be immobilized to the particle via a spacer sequence, which may be, for example, a hydrocarbon group containing 1 or more but 10 or less carbon atoms.

Immobilization of the nucleic acid probe specifically bindable with a nucleic acid including the intended base sequence to the particle via a covalent bond may be performed by, for example, introducing a functional group into the nucleic acid probe specifically bindable with a nucleic acid including the intended base sequence, and introducing a functional group having reactivity with the functional group into the surface of the particle to allow both of the functional groups to undergo reaction. For example, an amino group may be introduced into the nucleic acid probe specifically bindable with a nucleic acid including the intended base sequence, and an active ester group, an epoxy group, an aldehyde group, a carbodiimide group, an isothiocyanate group, or an isocyanate group may be introduced into the particle. This enables a covalent bond to be formed.

Further, a mercapto group may be introduced into the nucleic acid probe specifically bindable with a nucleic acid having an intended base sequence, and an active ester group, a maleimide group, or a disulfide group may be introduced into the particle.

Examples of the active ester group include a p-nitrophenyl group, a N-hydroxysuccinimide group, a succinimide group, a phthalic acid imide group, and a 5-norbornene-2,3-dicarboxyimide group.

Examples of the method for introducing a functional group into the surface of the particle include a method for treating the particle with a silane coupling agent containing a predetermined functional group.

Examples of the silane coupling agent include γ-aminopropyl triethoxysilane, N-β-(aminoethyl)-γ-aminopropyl trimethoxysilane, N-β-(aminoethyl)-β-aminopropylmethyl dimethoxysilane, and γ-glycidoxypropyl trimethoxysilane.

Another example of the method for introducing a functional group serving as a binding site into the particle is a plasma treatment. By such a plasma treatment, a functional group such as a hydroxyl group and an amino group can be introduced into the surface of a solid phase. The plasma treatment can be performed using an apparatus known to a person skilled in the art.

Example of a method for immobilizing the nucleic acid probe specifically bindable with a nucleic acid including the intended base sequence to the particle by physical adsorption include a method of electrostatically coupling the nucleic acid probe with the particle that is surface-treated with a polycation (for example, polylysine, polyallylamine, and polyethyleneimine), using charges of oligo (dT).

The shape of the dispersed phase is not particularly limited. Examples of the shape of the dispersed phase include a spherical shape.

When the dispersed phase is a liquid phase, it is preferable that the dispersed phase be a dispersed phase obtained by segmenting the solution described above into minute segments by a continuous phase.

The continuous phase refers to a liquid in which another liquid is dispersed in a dispersion system. Here, the continuous phase means the same as a dispersion medium, and means a liquid used for segmenting the solution into dispersed phases and conveying the segmented dispersed phases.

The continuous phase is not particularly limited and may be appropriately selected depending on the intended purpose so long as the continuous phase can segment the solution. For example, when the dispersed phases are aqueous, examples of the continuous phase include fluorocarbon-based oils and mineral oils.

In the case of segmenting an aqueous solution into dispersed phases using an oil-based continuous phase, it is preferable to add a surfactant in either the solution or the continuous phase. Addition of a surfactant makes it possible to improve stability of segmented dispersed phases.

The surfactant is not particularly limited and may be appropriately selected depending on the intended purpose. Examples of the surfactant include ionic surfactants and nonionic surfactants. One of these surfactants may be used alone or two or more of these surfactants may be used in combination.

Examples of the ionic surfactants include fatty acid sodium, fatty acid potassium, alpha-sulfo fatty acid ester sodium, sodium straight-chain alkyl benzene sulfonate, alkyl sulfuric acid ester sodium, alkyl ether sulfuric acid ester sodium, and sodium alpha-olefin sulfonate. One of these ionic surfactants may be used alone or two or more of these ionic surfactants may be used in combination.

Examples of the nonionic surfactants include alkyl glycoside, alkyl polyoxyethylene ether (e.g., BRIJ series), octyl phenol ethoxylate (e.g., TRITON X series, IGEPAL CA series, NONIDET P series, and NIKKOL OP series), polysorbates (e.g., TWEEN series such as TWEEN 20), sorbitan fatty acid esters, polyoxyethylene fatty acid esters, alkyl maltoside, sucrose fatty acid esters, glycoside fatty acid esters, glycerin fatty acid esters, propylene glycol fatty acid esters, and fatty acid monoglyceride. One of these nonionic surfactants may be used alone or two or more of these nonionic surfactants may be used in combination.

—Container—

The container is not particularly limited and may be appropriately selected depending on the intended purpose. Examples of the container include an openable container, a sealed container, and a nucleic acid sample-contained container having a particulate shape (a particulate container). Among these containers, a particulate container is preferable. When the container is a particulate container, the container can be a nucleic acid sample-contained container excellent in storage stability and handleability and including the intended base sequence in a known copy (unit) number.

The shape, size, volume, material, color, and number of the nucleic acid sample-contained container are not particularly limited and may be appropriately selected depending on the intended purpose.

The size of the nucleic acid sample-contained container is not particularly limited and may be appropriately selected depending on the intended purpose. For example, in the case of a particulate container, the length of the shorter axis is 0.1 mm or greater, preferably 0.3 mm, and more preferably 0.5 mm. When the length of the shorter axis of the particulate container is 0.1 mm or greater, the particulate container can be excellent in handleability such as pickability by a user.

The shape of the nucleic acid sample-contained container is not particularly limited and may be appropriately selected depending on the intended purpose so long as an amplifiable reagent can be located in the nucleic acid sample-contained container. Examples of the shape of the nucleic acid sample-contained container include concaves such as a flat bottom, a round bottom, a U bottom, and a V bottom, sections on a substrate, and a spherical shape.

The number of the concaves or sections of the nucleic acid sample-contained container is preferably a plural number of 2 or greater, more preferably 5 or greater, and yet more preferably 50 or greater.

As the nucleic acid sample-contained container, microtubes which are joined via a base material including 2 or more concaves or sections, or a multi-well plate can be suitably used.

Examples of the microtubes joined via a base material include a two-serial, three-serial, four-serial, six-serial, eight-serial, 12-serial, 16-serial, 24-serial, or 48-serial microtubes.

Examples of the multi-well plate include 24-well, 48-well, 96-well, 384-well, and 1,536-well plates.

The volume of the nucleic acid sample-contained container is not particularly limited and may be appropriately selected depending on the intended purpose. For example, when the nucleic acid sample-contained container is used as a reaction vessel of a nucleic acid testing device, the volume of the nucleic acid sample-contained container is preferably 10 microliters or greater but 1,000 microliters or less considering the amount of the sample. However, in the case of adding into a reaction system, a particulate container as the nucleic acid sample-contained container, the volume of the nucleic acid sample-contained container is 200 microliters or less, preferably 20 microliters or less, and more preferably 2 microliters or less. When the volume of the nucleic acid sample-contained container is 200 microliters or less, it is possible to suppress volume change of the reaction system into which the nucleic acid sample-contained container is added.

The material of the nucleic acid sample-contained container is not particularly limited and may be appropriately selected depending on the intended purpose. Examples of the material of the nucleic acid sample-contained container include insoluble and soluble materials.

Examples of the insoluble materials include polystyrene polypropylene, polyethylene, fluororesins, acrylic resins, polycarbonate, polyurethane, polyvinyl chloride, and polyethylene terephthalate.

Examples of the soluble materials include sodium alginate, agarose gel, and sugars.

Examples of the color of the nucleic acid sample-contained container include transparent colors, semi-transparent colors, chromatic colors, and complete light-shielding colors. When the nucleic acid sample-contained container is colored, the user can visually recognize information over the nucleic acid sample-contained container by the color and have improved handleability.

——Base Material——

It is preferable that the base material is a plate-shaped base material provided with the nucleic acid sample-contained container.

For example, the constituent material, shape, size, and structure of the base material are not particularly limited and may be appropriately selected depending on the intended purpose.

The constituent material of the base material is not particularly limited and may be appropriately selected depending on the intended purpose. Examples of the constituent material include semiconductors, ceramics, metals, glass, quartz glass, and plastics. Among these constituent materials, plastics are preferable.

Examples of the plastics include polystyrene, polypropylene, polyethylene, fluororesins, acrylic resins, polycarbonate, polyurethane, polyvinyl chloride, and polyethylene terephthalate.

The shape of the base material is not particularly limited and may be appropriately selected depending on the intended purpose. Examples of the shape of the base material include a board shape and a plate shape.

The structure of the base material is not particularly limited, may be appropriately selected depending on the intended purpose, and may be a single-layer structure or a multilayered structure.

——Particulate Shape——

Examples of the particulate container include a solid or gel particle that either has a shell encapsulating the first nucleic acid molecule and the second nucleic acid molecule, or contains the first nucleic acid molecule and the second nucleic acid molecule.

Examples of the shell encapsulating the first nucleic acid molecule and the second nucleic acid molecule include a capsule-shaped particle.

The nucleic acid sample-contained container of the present disclosure may include: a nucleic acid-containing dispersed phase containing the first nucleic acid molecule and the second nucleic acid molecule; a continuous phase; and a protective member encapsulating the dispersed phase and the continuous phase.

Examples of the solid particle include a tablet-shaped particle that contains in a dispersed state, dispersed phases containing a first nucleic acid molecule and a second nucleic acid molecule. Specific examples of the tablet-shaped particle include medical capsule, liposome, and microcapsule.

Examples of the gel particle include particles containing sodium alginate and agarose gel. Specific examples of the gel particle include artificial salmon roe.

The volume of the particulate container is not particularly limited, may be appropriately selected depending on the intended purpose, and, for example, is 200 microliters or less, preferably 20 microliters or less, and more preferably 2 microliters or less. When the volume of the particulate container is 200 microliters or less, it is possible to suppress volume change of the reaction system into which the particulate container is added.

For example, information on a nucleic acid contained in the nucleic acid sample-contained container and information on the dispersed phase may be applied on the nucleic acid sample-contained container.

The information on a nucleic acid contained in the nucleic acid sample-contained container is not particularly limited and may be appropriately selected depending on the intended purpose. Examples of the information include the sequence of the intended base sequence, the number of nucleic acid molecules including the intended base sequence, uncertainty of the number of nucleic acid molecules contained, and the kind of the nucleic acid. One of these kinds of information may be applied alone or two or more of these kinds of information may be applied in combination.

Examples of the information on the dispersed phase include the copy number of the nucleic acid dispensed, the kind of the solution in which the nucleic acid is dispersed, uncertainty of the dispersed phase, and filling accuracy of the dispersed phase. One of these kinds of information may be applied alone or two or more of these kinds of information may be applied in combination.

The average value and standard deviation of the copy number of the nucleic acid dispensed into a container can be obtained by calculating the average value and standard deviation of the copy number of the intended base sequence contained per positive dispersed phase according to the formula 1 to the formula 5 below. Using the formula 1 to the formula 5, it is possible to obtain the average value and standard deviation of the copy number of the intended base sequence contained per positive dispersed phase, taking into account a Poisson distribution.

$$P(X=k) = \left(\frac{e^{-\lambda}\lambda^k}{k!}\right) \Big/ \left(1 - \frac{e^{-\lambda}\lambda^0}{0!}\right) \ (k=1,2,3,\ldots,n) \quad \text{Formula 1}$$

$$\lambda = Posi/(Posi + Nega)$$

$$\overline{X} = \sum_{k=1}^{\infty}(k \cdot P(X=k)) \quad \text{Formula 2}$$

$$\sigma_1 = \sqrt{\sum_{k=1}^{\infty}\left[(k-\overline{X})^2 \cdot P(X=k)\right]} \quad \text{Formula 3}$$

$$m = N\overline{X} \ (N=1,2,3,\ldots n) \quad \text{Formula 4}$$

$$\sigma_m \sqrt{N} \cdot \sigma_1 \ (N=1,2,3,\ldots n) \quad \text{Formula 5}$$

In the formula 1, k represents the copy number contained per positive dispersed phase, X represents the ratio of positive dispersed phases (Posi) among all dispersed phases subjected to sample measurement, and P represents a probability of positive dispersed phases containing the intended base sequence in a predetermined copy number among all positive dispersed phases. The left-hand side of the formula 2 represents the average value of the copy number contained per positive dispersed phase. In the formula 3, $\sigma_1$ represents the standard deviation of the copy number contained per positive dispersed phase. In the formula 4 and the formula 5, N represents a specific segment number of segments which are positive dispersed phases, and m represents the average value of the copy number contained in the specific segment number of positive dispersed phases. In the formula 5, $\sigma_m$ represents the standard deviation of the copy number contained in the specific segment number of positive dispersed phases.

A positive dispersed phase refers to a dispersed phase from which a label in the dispersed phase is detected by a detecting device of a discharging mechanism to be described in the method of the present disclosure for producing a nucleic acid sample-contained container. A negative dispersed phase (Nega) refers to a dispersed phase from which a label in the dispersed phase is not detected by the detecting device of the discharging mechanism. When it is said that a label is not detected, it is meant that a threshold at which it is recognizable that a label is detected is not exceeded.

The probability at which only one intended base sequence is contained in positive dispersed phases is preferably 90% or higher. The probability at which only one intended base sequence is contained in positive dispersed phases refers to a probability at which only one intended base sequence is contained in positive dispersed phases among probabilities P of discrete copy numbers contained in respective dispersed phases.

"Uncertainty" is defined in ISO/IEC Guide 99:2007 [International Vocabulary of Metrology-Basics and general concepts and related terms (VIM)] as "a parameter that characterizes measurement result-incidental variation or dispersion of values rationally linkable to the measured quantity".

Here, "values rationally linkable to the measured quantity" means candidates for the true value of the measured quantity. That is, uncertainty means information on the variation of the results of measurement due to operations and devices involved in production of a measurement target. With a greater uncertainty, a greater variation is predicted in the results of measurement.

For example, the uncertainty may be standard deviation obtained from the results of measurement, or a half value of a reliability level, which is expressed as a numerical range in which the true value is contained at a predetermined probability or higher.

The uncertainty may be calculated according to the methods based on, for example, Guide to the Expression of Uncertainty in Measurement (GUM:ISO/IEC Guide 98-3), and Japan Accreditation Board Note 10, Guideline on Uncertainty in Measurement in Test. As the method for calculating the uncertainty, for example, there are two types of applicable methods: a type-A evaluation method using, for example, statistics of the measured values, and a type-B evaluation method using information on uncertainty obtained from, for example, calibration certificate, manufacturer's specification, and information open to the public.

All uncertainties due to factors such as operations and measurement can be expressed by the same reliability level, by conversion of the uncertainties to standard uncertainty. Standard uncertainty indicates variation in the average value of measured values.

In an example method for calculating the uncertainty, for example, factors that may cause uncertainties are extracted, and uncertainties (standard deviations) due to the respective factors are calculated. Then, the calculated uncertainties due to the respective factors are synthesized according to the sum-of-squares method, to calculate a synthesized standard uncertainty. In the calculation of the synthesized standard uncertainty, the sum-of-squares method is used. Therefore, a factor that causes a sufficiently small uncertainty can be ignored, among the factors that cause uncertainties. A coefficient of variation (CV value) obtained by dividing the synthesized standard uncertainty by an expected value may be used as the uncertainty.

The coefficient of variation means a relative value of the variation in the number of nucleic acids including the intended base sequence (or the number of nucleic acids) filled in each container (examples of the container including a particle and a well), where the variation occurs when nucleic acids including the intended base sequence are filled in the container. That is, the coefficient of variation means the filling accuracy in terms of the number of nucleic acids including the intended base sequence, filled in the container. The coefficient of variation is a value obtained by dividing standard deviation $\sigma$ by an average value x. Here, the coefficient of variation CV is assumed to be a value obtained by dividing standard deviation $\sigma$ by an average copy number (average number of copies filled) x. In this case, a relational expression represented by Formula 6 below is established.

$$CV = \frac{\sigma}{x} \qquad \text{Formula 6}$$

Generally, nucleic acids have a random distribution state of a Poisson distribution in a dispersion liquid. Therefore, in a random distribution state by a serial dilution method, i.e., of a Poisson distribution, standard deviation 6 can be regarded as satisfying a relational expression represented by Formula 7 below with an average copy number x. Hence, in the case where a dispersion liquid of nucleic acids is diluted by a serial dilution method, when coefficients of variation CV (CV value) for average copy numbers x are calculated according to Formula 8 below derived from Formula 6 above and Formula 7 based on the standard deviation 6 and the average copy numbers x, the results are as presented in Table 1 and FIG. 1. The coefficient of variation CV for a copy number having variation according to a Poisson distribution can be obtained from FIG. 1.

$$\sigma = \sqrt{x} \qquad \text{Formula 7}$$

$$CV = \frac{1}{\sqrt{x}} \qquad \text{Formula 8}$$

TABLE 1

| Average copy number x | Coefficient of variation CV |
|---|---|
| 1.00E+00 | 100.00% |
| 1.00E+01 | 31.62% |
| 1.00E+02 | 10.00% |
| 1.00E+03 | 3.16% |
| 1.00E+04 | 1.00% |
| 1.00E+05 | 0.32% |
| 1.00E+06 | 0.10% |

TABLE 1-continued

| Average copy number x | Coefficient of variation CV |
|---|---|
| 1.00E+07 | 0.03% |
| 1.00E+08 | 0.01% |

From the results of Table 1 and FIG. 1, it can be understood that when a container is to be filled with, for example, a copy number of 100 of nucleic acids by a serial dilution method, the final copy number of nucleic acids to be filled in the reaction solution has a coefficient of variation (CV) of at least 10%, even when other accuracies are ignored.

The filling accuracy (CV value) measured in terms of the number of intended base sequences to be contained in the nucleic acid sample-contained container is not particularly limited, may be appropriately selected depending on the intended purpose, and is preferably, for example, lower than 20%.

The method for applying information on the nucleic acid sample-contained container is not particularly limited and may be appropriately selected depending on the intended purpose. Examples of the method include a method of coloring the nucleic acid sample-contained container depending on the content of the information, and a method of printing the content of the information on a particle.

Use of the method of coloring the nucleic acid sample-contained container depending on the content of the information enables the user to visually recognize information on the nucleic acid sample-contained container and have improved handleability.

—Other Materials—

The other materials are not particularly limited and may be appropriately selected depending on the intended purpose. Examples of the other materials include a solution other than the solution of the dispersed phases, a fluorescent substance (a fluorescent labeling reagent), and a quencher.

The solution other than the solution of the dispersed phases is not particularly limited and may be appropriately selected depending on the intended purpose. Examples of the solution other than the solution of the dispersed phases include an oil based-solvent that does not dissolve nucleic acid.

Examples of the solution other than the solution of the dispersed phases include a protic polar solvent, an aprotic polar solvent, and a non-polar solvent.

The fluorescent substance (a fluorescent labeling reagent) is not particularly limited and may be appropriately selected depending on the intended purpose. Examples of the fluorescent substance include a fluorescent dye.

Examples of the fluorescent dye include fluoresceins, azo dyes, rhodamines, coumarins, pyrenes, and cyanines. One of these fluorescent dyes may be used alone or two or more of these fluorescent dyes may be used in combination. Among these fluorescent dyes, fluoresceins, azo dyes, and rhodamines are preferable, and particularly, SYBR GREEN, EVA GREEN, SYTOX GREEN, FAM, HEX, VIC (registered trademark), TEXAS RED (registered trademark), ROX, and FITC are more preferable.

The quencher is not particularly limited and may be appropriately selected depending on the intended purpose. Examples of the quencher include BHQ1, BHQ2, BHQ3, JOE, and TAMRA.

Figure 2:
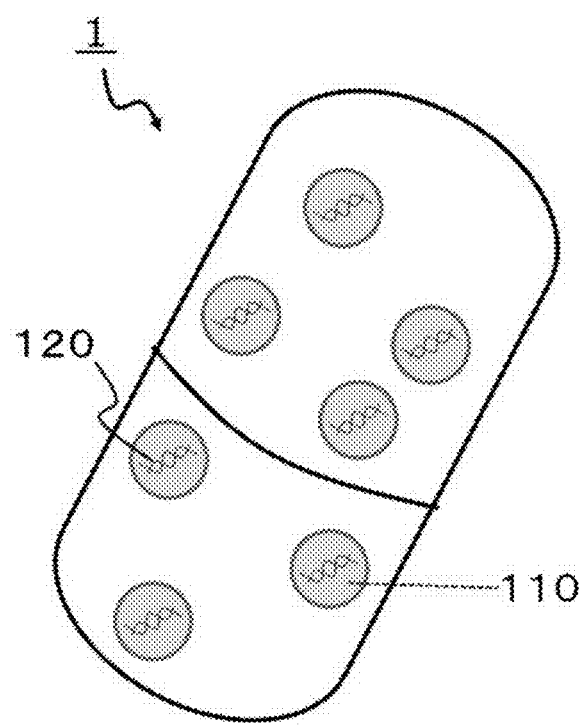
FIG. 2 is a diagram illustrating an example of a nucleic acid sample-contained container of the present disclosure.

FIG. 2 is a diagram illustrating an example of the nucleic acid sample-contained container of the present disclosure. FIG. 2 illustrates a capsule-shaped nucleic acid sample-contained container. However, the present disclosure is not limited to this form.

As illustrated in FIG. 2, a nucleic acid sample-contained container 1 encapsulates dispersed phases 110 containing a nucleic acid 120 including an intended base sequence. Further, as illustrated in FIG. 2, one dispersed phase 110 contains one nucleic acid molecule. Therefore, by controlling the number of dispersed phases 110 to be dispensed into the nucleic acid sample-contained container 1, it is possible to control the number of nucleic acids 120 that include an intended base sequence and are to be contained in the nucleic acid sample-contained container 1 to an arbitrary number.

Being formed as a particulate nucleic acid sample, the nucleic acid sample-contained container of the present disclosure can be improved in handleability. Because the nucleic acid sample has an improved handleability, it is possible to add a nucleic acid including an intended base sequence in a very trace needed amount in an arbitrary experiment system. This makes it possible to produce a reaction system suited to the requirement of a user. Here, a very trace amount refers to a number of molecules of about 1 molecule or greater but 1,000 molecules or less.

Further, because encapsulating nucleic acid samples in the particle, the nucleic acid sample-contained container of the present disclosure is excellent in storage stability of the nucleic acid.

Moreover, because the nucleic acid sample-contained container of the present disclosure can be strictly controlled in the copy (unit) number of the nucleic acid including an intended base sequence to be contained in the nucleic acid sample-contained container during production, it is possible to keep track of the copy (unit) number of the intended base sequence contained.

(Method and Apparatus for Producing Nucleic Acid Sample-Contained Container, and Non-Transitory Recording Medium Storing Program for Producing Nucleic Acid Sample-Contained Container)

An apparatus of the present disclosure configured to produce a nucleic acid sample-contained container operates as an apparatus configured to perform a method of the present disclosure for producing a nucleic acid sample-contained container by reading out and executing a program for producing a nucleic acid sample-contained container stored in a non-transitory recording medium of the present disclosure. That is, the apparatus of the present disclosure configured to produce a nucleic acid sample-contained container includes the non-transitory recording medium of the present disclosure storing a program for producing a nucleic acid sample-contained container and causing a computer to perform the same functions as the method of the present disclosure for producing a nucleic acid sample-contained container. The program for producing a nucleic acid sample-contained container stored in the non-transitory recording medium of the present disclosure is not limited to being executed by the apparatus of the present disclosure configured to produce a nucleic acid sample-contained container. For example, the program for producing a nucleic acid sample-contained container stored in the non-transitory recording medium of the present disclosure may be executed by any other computer or a server, or may be executed based on cooperation between any of the apparatus of the present disclosure configured to produce a nucleic acid sample-contained container, any other computer, and a server.

That is, the apparatus of the present disclosure configured to produce a nucleic acid sample-contained container is the same as carrying out the method of the present disclosure for producing a nucleic acid sample-contained container. Hence, the details of the method of the present disclosure for producing a nucleic acid sample-contained container will also be specified through description mainly about the apparatus of the present disclosure configured to produce a nucleic acid sample-contained container. Further, the non-transitory recording medium of the present disclosure storing the program for producing a nucleic acid sample-contained container realizes the apparatus of the present disclosure configured to produce a nucleic acid sample-contained container, with the use of, for example, computers as hardware resources. Hence, the details of the non-transitory recording medium of the present disclosure storing the program for producing a nucleic acid sample-contained container will also be specified through description of the apparatus of the present disclosure configured to produce a nucleic acid sample-contained container.

The method of the present disclosure for producing a nucleic acid sample-contained container includes a dispersed phase forming step of forming a plurality of dispersed phases containing a nucleic acid including an intended base sequence and a base sequence for detection different from the intended base sequence, an amplifying step of amplifying the base sequence for detection in the dispersed phases, a discriminating step of discriminating between positive dispersed phases in which the base sequence for detection has been amplified and negative dispersed phases in which the base sequence for detection has not been amplified among the dispersed phases, a sorting step of sorting from each other, the positive dispersed phases and the negative dispersed phases discriminated between in the discriminating step, and a dispensing step of dispensing the positive dispersed phases sorted in the sorting step into a container, and further includes other steps as needed.

The apparatus of the present disclosure configured to produce a nucleic acid sample-contained container includes a dispersed phase forming unit configured to form a plurality of dispersed phases containing a nucleic acid including an intended base sequence and a base sequence for detection different from the intended base sequence, an amplifying unit configured to amplify the base sequence for detection in the dispersed phases, a discriminating unit configured to discriminate between positive dispersed phases in which the base sequence for detection has been amplified and negative dispersed phases in which the base sequence for detection has not been amplified among the dispersed phases, a sorting unit configured to sort from each other, the positive dispersed phases and the negative dispersed phases discriminated between by the discriminating unit, and a dispensing unit configured to dispense the positive dispersed phases sorted by the sorting unit into a container, and further includes other units as needed.

The method of the present disclosure for producing a nucleic acid sample-contained container can be suitably performed by the apparatus configured to produce a nucleic acid sample-contained container. That is, the dispersed phase forming step can be suitably performed by the dispersed phase forming unit. The amplifying step can be suitably performed by the amplifying unit. The discriminating step can be suitably performed by the discriminating unit. The sorting step can be suitably performed by the sorting unit. The dispensing step can be suitably performed by the dispensing unit. The other steps can be suitably performed by the other units.

The present disclosure is based on a finding that the methods of the related art for producing a nucleic acid sample-contained container have difficulty dispensing a nucleic acid including an intended base sequence in a predetermined number into a container in a short time almost without inclusion of contaminants.

Specifically, for example, in the case of selecting a diluted solution containing a specific number of molecules based on a result of real-time PCR of diluted solutions of nucleic acid including the intended base sequence, the related art has a problem of difficulty producing and dispensing a standard reagent containing an arbitrary number of nucleic acid molecules. In this case, the time needed for producing a standard reagent and the amount by which the standard reagent can be produced are dependent on the performance of the device configured to perform real-time PCR. Hence, there may be a case where it is impossible to produce and dispense the standard reagent in a short time.

Moreover, for example, in the case of using cells into which an intended base sequence is introduced by a gene recombination technique, the related art has a problem of difficulty dispensing the nucleic acid in a short time, because there is a need for bothersome operations such as gene recombination and cell culture. In this case, there is a case where cell-attributed contaminants (for example, proteins and lipids) during isolation of the cells into which the intended base sequence has been introduced may contaminate the container into which the nucleic acid is dispensed.

Furthermore, the method of the related art for amplifying a portion of a nucleic acid having an intended base sequence and sorting (separating) a droplet or a gel droplet in which a nucleic acid amplification reaction has occurred may have difficulty dispensing the intended base sequence in a desired copy number (specific copy number).

The method of the present disclosure for producing a nucleic acid sample-contained container can dispense a nucleic acid including an intended base sequence in a predetermined number into a container in a short time with few contaminants.

<Dispersed Phase Forming Unit and Dispersed Phase Forming Step>

The dispersed phase forming unit is configured to form a plurality of dispersed phases containing a nucleic acid including an intended base sequence and a base sequence for detection different from the intended base sequence.

In the dispersed phase forming step, the dispersed phase forming unit forms a plurality of dispersed phases containing a nucleic acid including an intended base sequence and a base sequence for detection different from the intended base sequence.

The dispersed phase forming unit is not particularly limited and may be appropriately selected depending on the intended purpose so long as the dispersed phase forming unit can segment a nucleic acid-containing liquid described below to form a plurality of dispersed phases (so long as the dispersed phase forming unit can perform minute segmentation). Examples of the dispersed phase forming unit include a droplet generator. Examples of a measure for segmenting a nucleic acid-containing liquid into a plurality of dispersed phases rapidly include droplet generation using a micro-flow path and a method of filling a nucleic acid-containing liquid into micro/nano-scale wells.

As an apparatus configured to automatically form dispersed phases of a nucleic acid-containing liquid, for example, a droplet generator can be used.

As the droplet generator, a publicly known droplet generator can be used. Examples of the droplet generator include AUTOMATED DROPLET GENERATOR available from Bio-Rad Laboratories, K.K. and an emulsion (dispersed phase) producing apparatus described in Japanese Patent No. 3746766. The emulsion producing apparatus described in Japanese Patent No. 3746766 is configured to discharge dispersed phases in a direction crossing the flow of a continuous phase flowing through a micro-channel (micro-flow path), to produce dispersed phases by a shear force of the continuous phase.

It is also preferable to segment a solution more rapidly by passing a plurality of continuous splitters through the dispersed phases.

<<Nucleic Acid-Containing Liquid>>

The nucleic acid-containing liquid is not particularly limited and may be appropriately selected depending on the intended purpose. Description about the nucleic acid-containing liquid will be skipped because the same liquid as the solution used for the nucleic acid sample-contained container of the present disclosure can be used.

It is preferable that the nucleic acid-containing liquid contain a primer, a nucleic acid amplifying reagent, and a labeling reagent in order to have the base sequence for detection amplify in the amplifying step described below.

In the case of amplifying the base sequence for detection by a PCR method, the primer is an 18-mer through 30-mer synthetic oligonucleotide including a base sequence complementary with the base sequence for detection. A forward primer and a reverse primer are set at two positions in a manner to sandwich the region to be amplified.

Examples of the nucleic acid amplifying reagent include DNA polymerase, the four kinds of bases (dGTP, dCTP, &ATP, and dTTP), $Mg^{2+}$ (2 mM magnesium chloride), a buffer for maintaining the optimum pH (pH of from 7.5 through 9.5), dNTP, dUTP, Tris-HCl, and nuclease-free water.

With addition of the primer and the nucleic acid amplifying reagent for amplifying the base sequence for detection in the nucleic acid-containing liquid, it is possible to detect a dispersed phase as containing the intended base sequence in the discriminating step described below, without a change in the copy number of the intended base sequence contained in the dispersed phase.

The labeling reagent is not particularly limited and may be appropriately selected depending on the intended purpose, so long as the labeling reagent becomes identifiable as a label in response to amplification of the base sequence for detection. A labeling reagent that can apply an optical label (fluorescent label) to a dispersed phase is preferable. A reagent that applies an optical label is not particularly limited and may be appropriately selected depending on the intended purpose. Examples of the reagent that applies an optical label include nucleic acid probes such as Taq Man probe and Molecular Beacon and intercalators such as SYBR Green and Eva Green.

In the case of using an intercalator, it is possible to employ a method of adding the intercalator in the nucleic acid-containing liquid after the base sequence for detection is amplified.

<<Dispersed Phase>>

A dispersed phase refers to a small-sized unit into which the nucleic acid-containing liquid described above is segmented. Hereinafter, a dispersed phase may be referred to as "minute segment".

The dispersed phase refers to a region containing a nucleic acid including an intended base sequence, or a minute segment into which the nucleic acid-containing liquid in which nucleic acids including the intended base sequence are dispersed is segmented. Detailed description about the dispersed phase will be skipped because the dispersed phase is the same as the dispersed phase in the nucleic acid sample-contained container of the present disclosure.

In the case of segmenting a solution into dispersed phases using the dispersed phase forming unit, it is preferable to perform segmentation using a nucleic acid-containing liquid having a nucleic acid concentration at which at most one nucleic acid (one nucleic acid molecule) including the intended base sequence and the base sequence for detection before amplified will be contained per dispersed phase.

The nucleic acid concentration at which at most one nucleic acid molecule including the intended base sequence will be contained per dispersed phase is preferably a nucleic acid concentration at which the number of dispersed phases in which the nucleic acid including the intended base sequence is contained will be one dispersed phase out of from ten through a hundred dispersed phases.

With the solution set to the nucleic acid concentration at which the number of dispersed phases in which the nucleic acid including the intended base sequence is to be contained will be one dispersed phase, it is expected that the number of nucleic acids to be contained in a dispersed phase will be zero molecules (no nucleic acid contained) or one molecule. This makes it possible to more accurately control the number of nucleic acid molecules to be dispensed during dispensing of dispersed phases by the dispensing unit described below.

——Nucleic Acid——

Description about the nucleic acid will be skipped because the same nucleic acid as can be used in the nucleic acid sample-contained container of the present disclosure can be used.

——Intended Base Sequence——

The intended base sequence is not particularly limited and may be appropriately selected depending on the intended purpose. Description about the intended base sequence will be skipped because the same base sequence as can be used in the nucleic acid sample-contained container of the present disclosure can be used.

In the present disclosure, the number of the very intended base sequences is also referred to as copy number. Further, one continuous nucleic acid including this intended base sequence and any other base sequence (for example, the base sequence for detection described below) is, as one unit, referred to as one molecule, for example. In the present disclosure, it is preferable that the copy number of the intended base sequence to be included in one nucleic acid molecule be one. Moreover, in the present disclosure, because the base sequence for detection described below will be amplified in the nucleic acid including the intended base sequence and the base sequence for detection, there is no change in the copy number of the intended base sequence between before and after amplification.

——Base Sequence for Detection——

The base sequence for detection is not particularly limited and may be appropriately selected depending on the intended purpose. Description about the base sequence for detection will be skipped because the same base sequence as can be used in the nucleic acid sample-contained container of the present disclosure can be used.

<Amplifying Unit and Amplifying Step>

The amplifying unit is configured to amplify the base sequence for detection in a dispersed phase.

In the amplifying step, the amplifying unit amplifies the base sequence for detection in a dispersed phase.

The amplifying unit is not particularly limited and may be appropriately selected depending on the intended purpose so long as the amplifying unit can perform accurate temperature control. Examples of the amplifying unit include a thermal cycler, a real-time PCR device, and a hot plate.

The method for amplifying the base sequence for detection is not particularly limited and may be appropriately selected depending on the intended purpose. Examples of the method include a PCR method and an isothermal amplification method.

Examples of the isothermal amplification method include an NASBA method, a LAMP method, an RCA method, a SMAP method, an RPA method, and an HCR method.

In the case of using the RCA method, for example, first, a nucleic acid including the base sequence for detection disposed at the 3' terminal is circularized using a probe having a base sequence complementary with the base sequences at the 3' terminal and the 5' terminal and is allowed to undergo a ligation reaction, to obtain a cyclic nucleic acid. Next, using an elongation reaction primer for the obtained cyclic shape, the nucleic acid fragment including the base sequence for detection can be amplified.

It is also possible to perform a nucleic acid amplification reaction using a cyclic probe previously circularized and including a base sequence complementary with the base sequence for detection disposed at the 3' terminal. In this case, it is preferable to use a label such as a probe specifically bindable with the base sequence for detection, as an optical labeling reagent described below.

The amplifying unit may be configured to amplify the base sequence for detection contained in a dispersed phase on a micro-flow path, or may be configured to amplify the base sequence for detection contained in a dispersed phase that is distributed into a tube.

The amplifying unit can accurately control the number of nucleic acid molecules including the intended base sequence and contained in a dispersed phase, by amplifying the base sequence for detection in the dispersed phase. For example, it is assumed that a dispersed phase before amplification of the base sequence for detection by the amplifying unit contains one nucleic acid molecule including one copy of the intended base sequence. In this case, the copy number of the intended base sequence contained in the dispersed phase after amplification of the base sequence for detection by the amplifying unit remains one copy, which is the same as before amplification. The dispensing unit described below can dispense the intended base sequence in a desired copy number (in a predetermined number) into, for example, a container described below, by dispensing the dispersed phase containing the nucleic acid including the intended base sequence in a specified copy number.

<Discriminating Unit and Discriminating Step>

The discriminating unit is configured to discriminate between dispersed phases (positive dispersed phases) in which the base sequence for detection has been amplified and dispersed phases (negative dispersed phases) in which the base sequence for detection has not been amplified among the dispersed phases.

In the discriminating step, the discriminating unit discriminates between dispersed phases (positive dispersed phases) in which the base sequence for detection has been amplified and dispersed phases (negative dispersed phases) in which the base sequence for detection has not been amplified among the dispersed phases.

The discriminating unit is not particularly limited and may be appropriately selected depending on the intended purpose. For example, when a labeling reagent for applying an optical label is contained in a dispersed phase, examples of the discriminating unit include an optical discriminating unit including a light source and a light receiving element.

When the discriminating unit is an optical discriminating unit, the discriminating unit can detect a light signal emitted by a dispersed phase and discriminate a dispersed phase containing a nucleic acid in which the base sequence for detection has been amplified. Examples of a specific discriminating method of the optical discriminating unit include a method of setting a threshold for the intensity of the light signal emitted by a dispersed phase and discriminating that the dispersed phase contains the nucleic acid including the intended base sequence when the intensity of the detected light signal is higher than the threshold.

The optical discriminating unit is not particularly limited and may be appropriately selected depending on the intended purpose, so long as the optical discriminating unit is configured to irradiate a dispersed phase with light from a light source and includes a light receiving element capable of detecting a light signal corresponding to the irradiation light from the dispersed phase.

The light source is not particularly limited and may be appropriately selected depending on the intended purpose, so long as the light source can excite a light signal from a dispersed phase. It is possible to use, for example, an ordinary lamp such as a mercury lamp and a halogen lamp to which a filter is applied for emission of a specific wavelength, a LED (Light Emitting Diode), and a laser. However, particularly when forming a minute liquid droplet of 1 nL or less, there is a need for irradiating a small region with a high light intensity. Therefore, use of a laser is preferable. As a laser light source, various commonly known lasers such as a solid-state laser, a gas laser, and a semiconductor laser can be used.

The light receiving element is not particularly limited and may be appropriately selected depending on the intended purpose so long as the light receiving element is an element capable of receiving a light signal emitted by a dispersed phase. An optical sensor configured to receive a light signal from a dispersed phase in a liquid droplet when the liquid droplet is irradiated with light having a specific wavelength is preferable. Examples of the light receiving element include one-dimensional elements such as a photodiode and a photosensor. When high-sensitivity measurement is needed, it is preferable to use a photomultiplier tube and an Avalanche photodiode. As the light receiving element, two-dimensional elements such as a CCD (Charge Coupled Device), a CMOS (Complementary Metal Oxide Semiconductor), and a gate CCD may also be used.

It is preferable that the discriminating unit count the number of positive dispersed phases at the same time as discriminating between positive dispersed phases in which the base sequence for detection has been amplified and negative dispersed phases in which the base sequence for detection has not been amplified among the dispersed phases. By the discriminating unit counting the number of positive dispersed phases at the same time as discriminating between positive dispersed phases and negative dispersed phases, it is possible to adjust the number of positive dispersed phases to be dispensed in the dispensing step described below.

<Sorting Unit and Sorting Step>

The sorting unit is configured to sort from each other, the positive dispersed phases and the negative dispersed phases discriminated between by the discriminating unit.

In the sorting step, the sorting unit sorts from each other, the positive dispersed phases and the negative dispersed phases discriminated between in the discriminating step.

The sorting unit is not particularly limited and may be appropriately selected depending on the intended purpose. Examples of the sorting unit include electrodynamic mechanism, a mechanism configured to deform a flow path to control the flow of a fluid, and a mechanism using a mechanical valve.

When the sorting unit is an electrodynamic mechanism, the sorting unit can sort the positive dispersed phases at a high speed. Examples of a specific electrodynamic mechanism include a method of forming a non-uniform electric field and attracting only target dispersed phases by dielectrophoresis.

Further, by synchronizing the sorting with the light signal detected by the discriminating unit in the discriminating step, it is possible to sort the dispersed phases in a suitable manner.

It is preferable that the positive dispersed phases sorted by the sorting unit be conveyed to a dispensing mechanism described below.

<Dispensing Unit and Dispensing Step>

The dispensing unit is configured to dispense into a container, a positive dispersed phase that is sorted by the sorting unit.

In the dispensing step, the dispensing unit dispenses into a container, a positive dispersed phase that is sorted in the sorting step.

The dispensing unit includes a discharging mechanism configured for dispensing into a container.

The discharging mechanism is configured to dispense a dispersed phase containing a nucleic acid including the intended base sequence and sorted by a sorting mechanism, into a container.

The discharging mechanism is not particularly limited and may be appropriately selected depending on the intended purpose. Examples of the discharging mechanism include a flow path capable of conveying a dispersed phase to a container, an on-demand type discharging mechanism, and a continuous type discharging mechanism. Among these discharging mechanisms, a flow path capable of conveying a dispersed phase to a container is preferable.

The flow path capable of conveying a dispersed phase to a container is not particularly limited and may be appropriately selected depending on the intended purpose. Examples of the flow path include a tube capable of conveying a dispersed phase.

Examples of the on-demand type discharging mechanism include a discharging head.

Examples of the type of the discharging head include an inkjet type.

Examples of the inkjet type discharging head include a pressure applying type, a thermal type, and an electrostatic type. Among these inkjet type discharging heads, the pressure applying type is preferable for the reason described below.

In the electrostatic type, there is a need for disposing an electrode in a manner to face the discharging mechanism that is configured to retain dispersed phases and form liquid droplets. In the apparatus of the present disclosure configured to produce a nucleic acid sample-contained container, there may be a case where the discharging mechanism is disposed in a manner to face a container. Hence, it is preferable not to provide an electrode, in order to increase the degree of latitude in locating the dispersed phases.

In the thermal type, there are a risk of local heating concentration that may affect the nucleic acids, which are a biomaterial, and a risk of kogation to the heater portion. Influences by heat depend on the components contained in the dispersed phases or the purpose for which the dispensed product is used. Therefore, there is no need for flatly rejecting the thermal method. However, the pressure applying type is preferable because the pressure applying type has a lower risk of kogation to the heater portion than the thermal type.

Examples of the pressure applying type include a type of applying a pressure to a liquid using a piezo element, and a type of applying a pressure using a valve such as an electromagnetic valve.

The discharging mechanism may further include a detecting device capable of detecting a label contained in a dispersed phase.

The detecting device is not particularly limited and may be appropriately selected depending on the intended purpose. The same device as an optical amplification detecting mechanism (discriminating unit) can be used.

The above-described various processes performed by the apparatus configured to produce a nucleic acid sample-contained container are performed by a computer including a control unit constituting the apparatus configured to produce a nucleic acid sample-contained container.

The computer is not particularly limited and may be appropriately selected depending on the intended purpose so long as the computer is a device including devices for, for example, memory, computing, and control. Examples of the computer include a personal computer.

The nucleic acid sample-contained container produced by the apparatus of the present disclosure configured to produce a nucleic acid sample-contained container is controlled in the copy (unit) number of the intended base sequence dispensed in the container. Therefore, the container can be suitably used for, for example, food inspection and blood tests. Examples of the container include a particle and a plate in which wells are formed and that is commonly used in the biotechnological field. The number of wells in the plate is not particularly limited, may be appropriately selected depending on the intended purpose, and may be a singular number or a plural number.

The particle is not particularly limited and may be appropriately selected depending on the intended purpose. Examples of the particle include the particle that is described in the description of the nucleic acid sample-contained container of the present disclosure.

As the plate, it is preferable to use, for example, a 1-well microtube, 8-series tubes, a 96-well plate, and a 384-well plate. When the number of wells is a plural number, it is possible to dispense the same number of nucleic acids into the wells of these plates, or it is also possible to dispense numbers of nucleic acids of different levels into the wells. There may be a well in which no nucleic acids are contained. Particularly, for producing a plate used for evaluating a real-time PCR device or digital PCR device configured to quantitatively evaluate an amount of nucleic acids, it is preferable to dispense numbers of nucleic acids of a plurality of levels. For example, it is conceivable to produce a plate into which nucleic acids are dispensed at 7 levels, namely about 1 nucleic acid, 2 nucleic acids, 4 nucleic acids, 8 nucleic acids, 16 nucleic acids, 32 nucleic acids, and 64 nucleic acids. Using such a plate, it is possible to inspect, for example, quantitativity, linearity, and lower limit of evaluation of a real-time PCR device or digital PCR device. Besides, it is possible to use such a plate as a reference for expression level analyses of a next-generation sequencer.

An aqueous liquid may be previously filled in a well.

Examples of the aqueous liquid to be filled in a well include nuclease-free water, a nucleic acid amplifying reagent, and a nucleic acid preservative reagent. By filling an aqueous liquid in a well, it is possible to use the nucleic acid sample for the next reaction immediately.

<Other Units and Other Steps>

The other steps are not particularly limited and may be appropriately selected depending on the intended purpose. Examples of the other steps include a counting step.

The counting step can be suitably performed by a counting unit.

The counting unit may be configured to count the number of dispersed phases in a flow path provided between the sorting mechanism and the discharging mechanism described above, may be configured to count the number of dispersed phases in the discharging mechanism, or may be configured to count the number of dispersed phases discharged by the discharging mechanism. In the case of counting the number of dispersed phases discharged by the discharging mechanism, the counting unit counts the number of dispersed phases contained in a liquid droplet of a continuous phase discharged by the discharging mechanism.

The counting unit is not particularly limited and may be appropriately selected depending on the intended purpose. For example, when an optical label (fluorescent label) is used as a labeling reagent, examples of the counting unit include an optical counting mechanism including a light source and a light receiving element.

The optical counting mechanism is not particularly limited and may be appropriately selected depending on the intended purpose. The same mechanism as the optical amplification detecting mechanism (discriminating unit) can be used.

In the case of counting the number of dispersed phases contained in a liquid droplet of a continuous phase discharged by the discharging mechanism, irradiation light to be emitted by the optical counting mechanism is preferably configured for continuous irradiation of a region through which the liquid droplet passes, or for pulsed irradiation of the region in synchronization with discharging of the liquid droplet at a timing delayed by a predetermined period of time from the operation for discharging the liquid droplet, in order to count the number of dispersed phases contained in the flying liquid droplet.

By the counting unit counting the number of dispersed phases contained in a liquid droplet of a nucleic acid-containing liquid discharged, it is possible to specify the number of dispersed phases contained in the liquid droplet actually discharged. This makes it possible to accurately control the number of dispersed phases to be dispensed into a container.

The method of the present disclosure for producing a nucleic acid sample-contained container is not a method of dispensing nucleic acids by a method of isolating cells after the cells including the nucleic acids are dispensed, but is a method of dispensing nucleic acids without cells. Therefore, inclusion of, for example, contaminants attributable to the cells (for example, proteins and lipids) into the reaction system can be prevented.

The method of the present disclosure for producing a nucleic acid sample-contained container will be described below in detail with reference to the drawings. The following description will be given, taking for example, a case of segmenting a nucleic acid-containing liquid using a micro-flow path to form dispersed phases.

Figure 3:
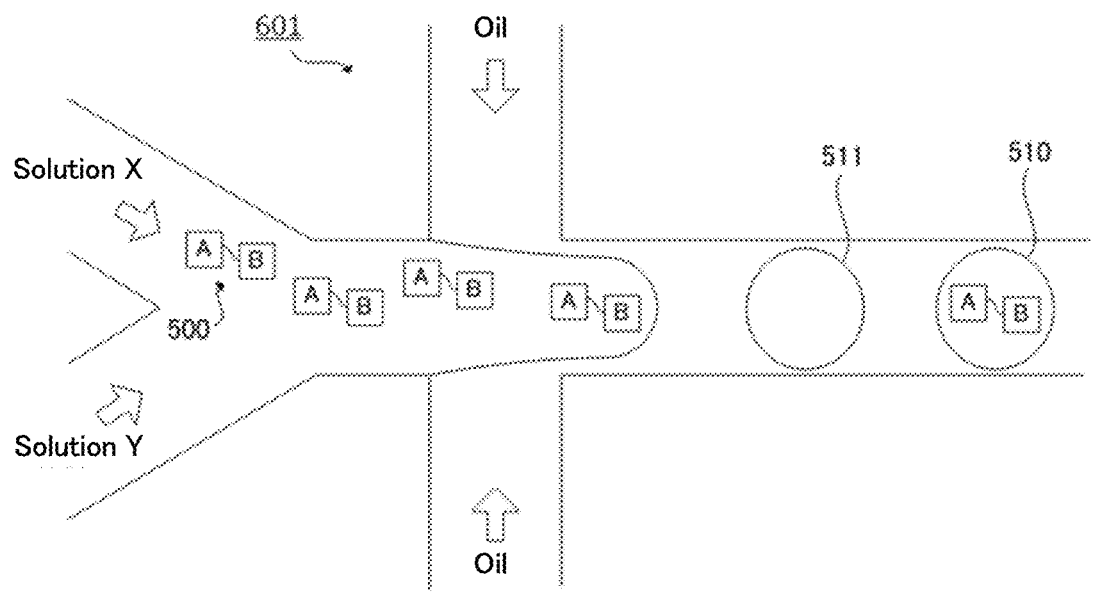
FIG. 3 is a diagram illustrating an example of a dispersed phase forming unit configured to segment a solution into dispersed phases in a micro-flow path.

FIG. 3 is a diagram illustrating an example of a dispersed phase forming unit configured to segment a solution X, which is a nucleic acid-containing liquid, into dispersed phases in a micro-flow path.

As illustrated in FIG. 3, a solution X containing nucleic acids 500 including an intended base sequence A and a base sequence for detection B for confirming the presence of the intended base sequence A flows through a flow path provided at the upper left portion of a dispersed phase forming unit 601. A solution Y containing a nucleic acid amplifying reagent and a fluorescent labeling reagent flows through a flow path provided at the lower left portion of the dispersed phase forming unit 601. The solution X and the solution Y meet each other in one flow path and mix with each other.

In the case of mixing the solution X and the solution Y in a micro-flow path, it is possible to provide a flow path capable of stirring the solution X and the solution Y after the two flow paths merge into one flow path. Examples of the flow path capable of stirring the solution X and the solution Y include a meandering flow path, a pillar array flow path, a broadening flow path, and a tapering flow path.

Next, the mixture liquid obtained from mixing of the solution X and the solution Y is segmented into droplet-shaped dispersed phases by a shear force from an oil, which is a continuous-phase fluid flowing from above and below the center portion of FIG. 3, and conveyed to the downstream side (right-hand side) of the flow path in FIG. 3.

In FIG. 3, a solution having a nucleic acid concentration at which at most one nucleic acid molecule 500 is contained per dispersed phase is used. Therefore, a dispersed phase 510 containing one nucleic acid molecule 500 and a dispersed phase 511 containing no nucleic acid 500 are formed.

Use of a micro-flow path as the dispersed phase forming unit 601 makes it possible to extremely rapidly segment the mixture liquid of the solution X and the solution Y into dispersed phases. Specifically, by segmenting the nucleic acid-containing liquid into dispersed phases using a micro-flow path, it is possible to form dispersed phases rapidly at a rate of about 1,000 dispersed phases per second.

Figure 4:
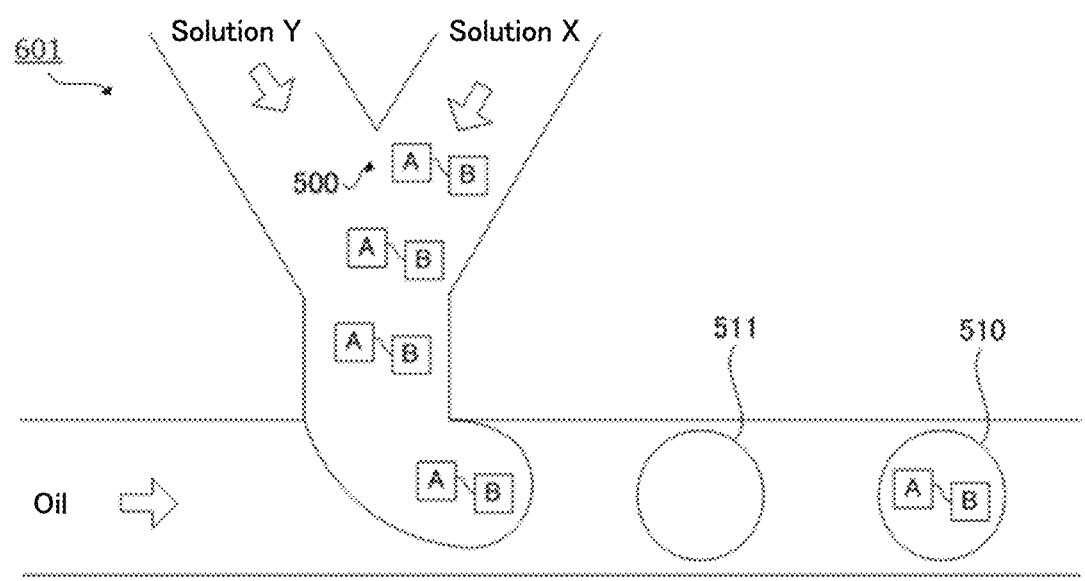
FIG. 4 is a diagram illustrating another example of a dispersed phase forming unit configured to segment a solution into dispersed phases in a micro-flow path.

FIG. 4 is a diagram illustrating another example of a dispersed phase forming unit configured to segment the solution X into dispersed phases in a micro-flow path.

A solution X, which is a nucleic acid-containing liquid containing nucleic acids 500 including an intended base sequence A and a base sequence for detection B for confirming the presence of the intended base sequence A flows through a flow path provided at the upper right portion of a dispersed phase forming unit 601. A solution Y containing a nucleic acid amplifying reagent and a fluorescent labeling reagent flows through a flow path provided at the upper left portion of the dispersed phase forming unit 601. The solution X and the solution Y meet each other in one flow path and mix with each other.

Next, the mixture liquid of the mixed solution X and solution Y is segmented into droplet-shaped dispersed phases by a shear force from an oil, which is a continuous-phase fluid flowing from the lower left portion of the center portion of the dispersed phase forming unit 601, and conveyed to the downstream side of the flow path at the right-hand side of FIG. 4.

Figure 5:
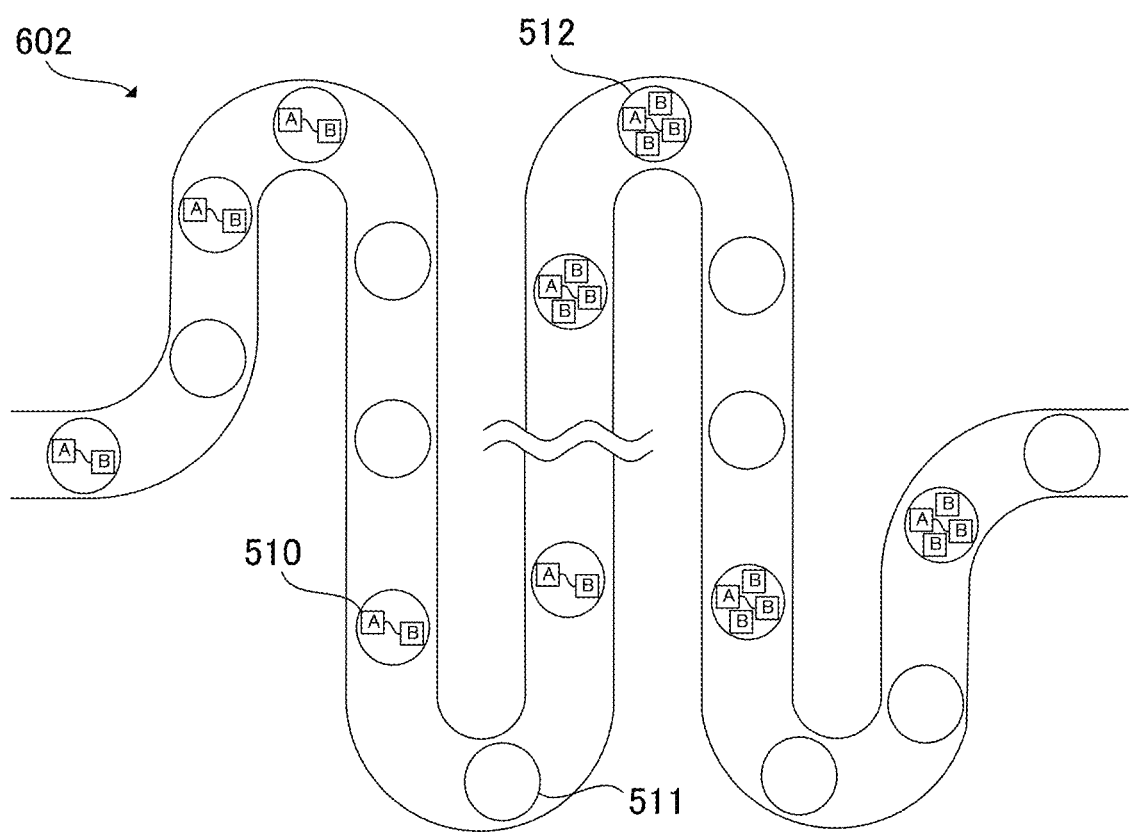
FIG. 5 is a diagram illustrating an example of an amplifying unit.

FIG. 5 is a diagram illustrating an example of an amplifying unit.

An amplifying unit 602 is configured to allow a dispersed phase 510 containing a nucleic acid 500 to undergo a nucleic acid amplification reaction according to a PCR method, to amplify a base sequence for detection B included in the nucleic acid 500 and optically label the dispersed phase 510.

Specifically, the amplifying unit 602 is configured to raise and drop the temperature of a dispersed phase 510 containing a nucleic acid 500, a nucleic acid amplifying reagent, and a fluorescent labeling reagent by flowing the dispersed phase 510 through a meandering flow path having a plurality of temperature ranges. By the dispersed phase 510 rising and falling between the plurality of temperature ranges, the base sequence for detection B in the nucleic acid 500 contained in the dispersed phase 510 is amplified by the nucleic acid amplifying reagent. As a result, the dispersed phase 510 becomes a dispersed phase 512 containing the nucleic acid 500 in which the base sequence for detection B has been amplified. Then, in response to the amplification of the base sequence for detection B, the fluorescent labeling reagent reacts with the base sequence for detection B in the dispersed phase 512, to bring the dispersed phase 512 into an optically labeled state.

Figure 6:
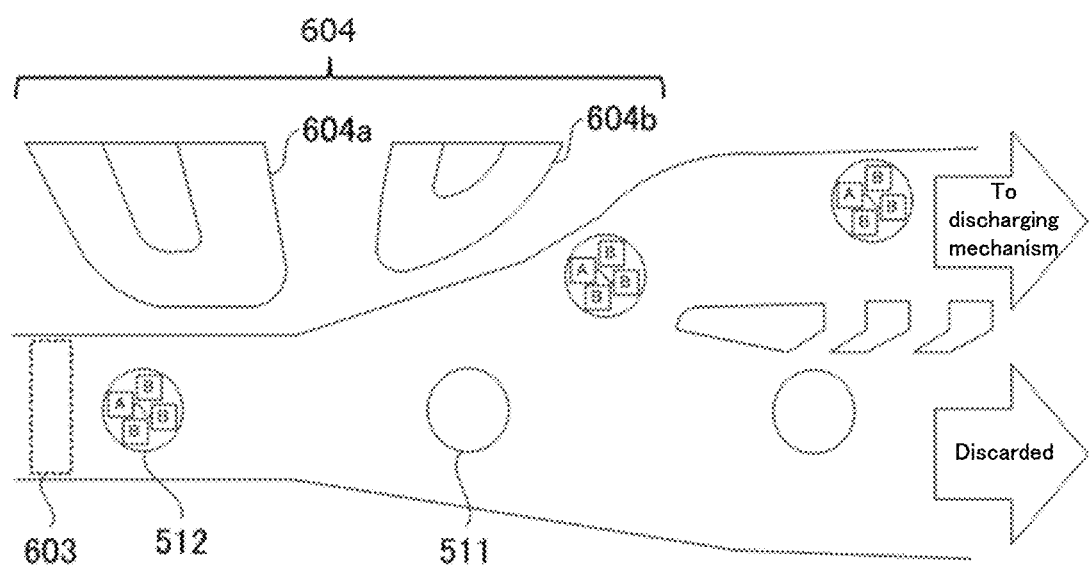
FIG. 6 is a diagram illustrating an example of a discriminating unit and a sorting mechanism of a sorting unit.

The optically labeled dispersed phase 512 emits fluorescence at a higher intensity than a dispersed phase 511 containing no nucleic acid 500 when irradiated with light from the light source of the discriminating unit 603 illustrated in FIG. 6. This makes it easy to discriminate between the optically labeled dispersed phase 512 and the dispersed phase 511 containing no nucleic acid 500.

FIG. 6 is a diagram illustrating an example of a discriminating unit configured to discriminate a dispersed phase containing a nucleic acid in which the base sequence for detection B has been amplified, and a discriminating mechanism and a sorting mechanism of the sorting unit configured to sort the dispersed phases by dielectrophoresis.

A discriminating unit 603 is configured to detect fluorescence from a dispersed phase 512 in which the base sequence for detection B has been amplified, and discriminate between the dispersed phase 512 containing a nucleic acid 500 in which the base sequence for detection B has been amplified and a dispersed phase 511 containing no nucleic acid 500.

When an optical detection mechanism of the discriminating unit 603 performs fluorescence detection, the optical detection mechanism includes a light source and a light receiving element. The light receiving element is configured to receive fluorescence, which the dispersed phase 512 being in an optically labeled state as a result of the base sequence for detection B having been amplified, emits in response to absorbing light from the light source as excitation light. Because the fluorescence is emitted to all directions from the dispersed phase 512, the light receiving element can be disposed at an arbitrary position at which the fluorescence is receivable. Here, in order to improve contrast, it is preferable to dispose the light receiving element at a position at which direct incidence of the light emitted by the light source to the light receiving element does not occur.

The discriminating unit 603 is configured to discriminate between the dispersed phase 512 containing a nucleic acid in which the base sequence for detection B has been amplified and the dispersed phase 511 containing no nucleic acid 500 based on the intensity of the fluorescence received by the light receiving element.

A sorting mechanism 604 including a cathode 604a and an anode 604b is configured to sort a dispersed phase 512 containing a nucleic acid in which the base sequence for detection B has been amplified, and a dispersed phase 511 containing no nucleic acid 500 by dielectrophoresis.

The sorting mechanism 604 is configured to form a non-uniform electric field around the sorting mechanism 604 by applying an appropriate voltage to the cathode 604a and the anode 604b illustrated in the upper section of FIG. 6, when the dispersed phase 512 containing a nucleic acid 500 in which the base sequence for detection B has been amplified passes by the sorting mechanism 604. The dispersed phase 512 polarized by the non-uniform electric field undergoes dielectrophoresis under the non-uniform electric field to be attracted toward the sorting mechanism 604 and flows through a flow path provided at the upper right portion of FIG. 6, to be conveyed to the discharging mechanism.

The sorting mechanism 604 is configured not to apply a voltage to the cathode 604a and the anode 604b when the dispersed phase 511 containing no nucleic acid 500 passes by the sorting mechanism 604. Hence, the dispersed phase 511 containing no nucleic acid 500 does not undergo dielectrophoresis but flows into a flow path provided at the lower right portion of FIG. 6, to be discarded.

Here, it is preferable that the flow path through which the dispersed phase 512 in which the base sequence for detection B has been amplified and that is sorted by the sorting mechanism 604 flows have a fluid resistance that is from 1.2 times through 1.5 times higher than the fluid resistance of the discarding flow path through which the dispersed phase 511 containing no nucleic acid 500 flows. At the mentioned fluid resistance, all dispersed phases flow into the discarding flow path when no electric field is applied. Hence, more secure sorting of dispersed phases 512 containing a nucleic acid in which the base sequence for detection B has been amplified can be realized.

Figure 7:
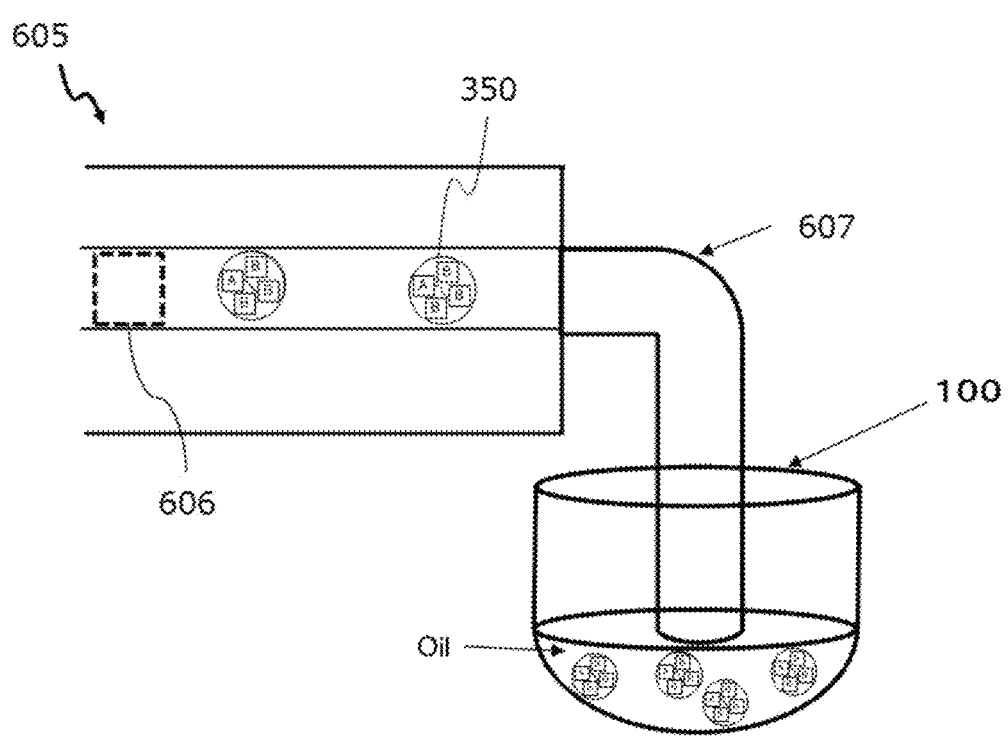
FIG. 7 is a diagram illustrating an example of a discharging mechanism of a dispensing unit.

FIG. 7 is a diagram illustrating an example of a discharging mechanism.

As illustrated in FIG. 7, a discharging mechanism 605 includes a detecting mechanism 606 that is the same as the discriminating unit 603, and a flow path 607 capable of conveying a dispersed phase. In the following description, the dispersed phase 512 containing a nucleic acid in which the base sequence for detection B has been amplified may be referred to as sorted dispersed phase 350.

As illustrated in FIG. 7, the discharging mechanism 605 is dispensing the dispersed phase 350 sorted by the sorting mechanism 604 into a capsule 100. Here, the number of dispersed phases 350 to be dispensed into the capsule 100 is controlled based on the label detected by the detecting mechanism 606.

Next, a case of dispensing dispersed phases into a container using an inkjet-type discharging mechanism as a dispensing unit of the method of the present disclosure for producing a nucleic acid sample-contained container will be described with reference to the drawings. Description of the process up to sorting of dispersed phases illustrated in FIG. 3 to FIG. 6 will be skipped, because the process up to the sorting is the same as in the case of segmenting a nucleic acid-containing liquid using a micro-flow path to form dispersed phases.

Figure 8:
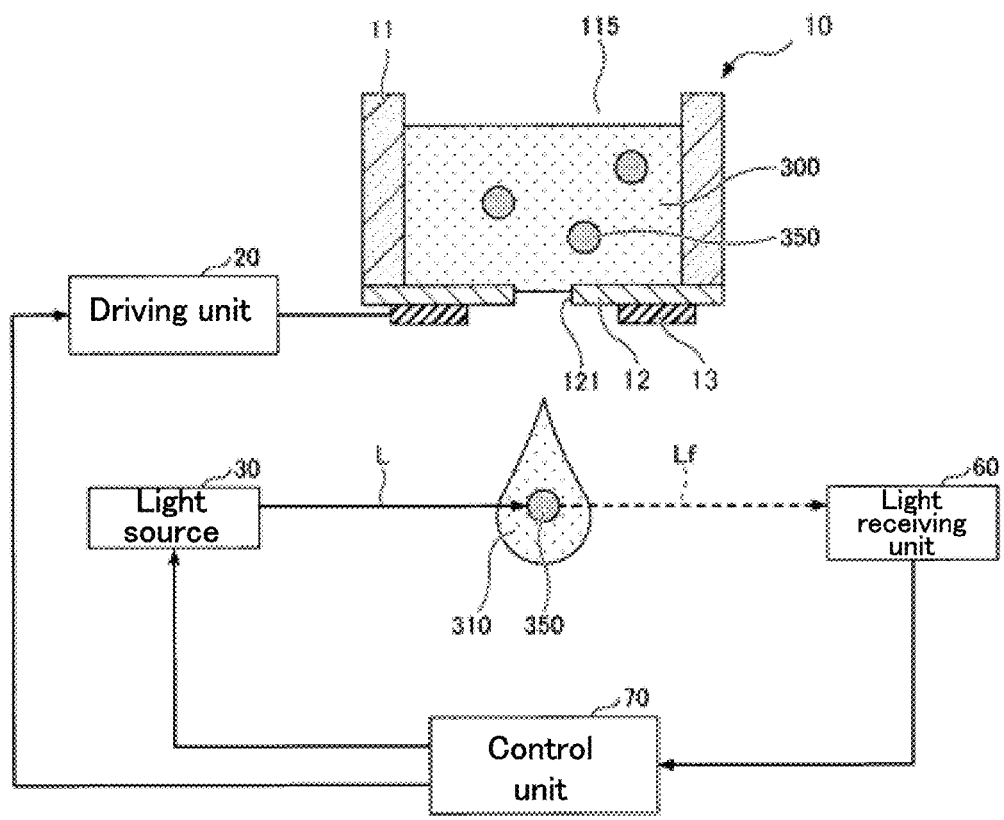
FIG. 8 is a diagram illustrating an embodiment of a discharging mechanism of a dispensing unit and a counting mechanism.

FIG. 8 is a diagram illustrating an embodiment of a discharging mechanism and a counting mechanism.

The discharging mechanism 10 includes a liquid chamber 11, a membrane 12, and a driving element 13. At the top, the liquid chamber 11 has an atmospherically exposed portion 115 configured to expose the interior of the liquid chamber 11 to the atmosphere, and bubbles mixed in an oil 300 can be evacuated through the atmospherically exposed portion 115. In the following description, a dispersed phase 512 containing a nucleic acid in which the base sequence for detection B has been amplified may be referred to as sorted dispersed phase 350.

The membrane 12 is a film-shaped member secured at the lower end of the liquid chamber 11. A nozzle 121, which is a through hole, is formed in approximately the center of the membrane 12, and the vibration of the membrane 12 causes the oil 300 retained in the liquid chamber 11 to be discharged through the nozzle 121 in the form of a liquid droplet 310. Because the liquid droplet 310 is formed by the inertia of the vibration of the membrane 12, it is possible to discharge the oil 300 even when the oil 300 has a high surface tension (a high viscosity). The planer shape of the membrane 12 may be, for example, a circular shape, but may also be, for example, an elliptic shape or a quadrangular shape.

The material of the membrane 12 is not particularly limited. However, if the material of the membrane 12 is extremely flexible, the membrane 12 easily undergo vibration and is not easily able to stop vibration immediately when there is no need for discharging. Therefore, a material having a certain degree of hardness is preferable. As the material of the membrane 12, for example, a metal material, a ceramic material, and a polymeric material having a certain degree of hardness can be used.

It is preferable that the nozzle 121 be formed as a through hole having a substantially perfect circle shape in approximately the center of the membrane 12. In this case, the diameter of the nozzle 121 is not particularly limited but is preferably two times or more greater than the size of the sorted dispersed phase 350 in order to prevent the nozzle 121 from being clogged with the sorted dispersed phase 350.

On the other hand, when a liquid droplet is extremely large, it is difficult to achieve an object of forming a minute liquid droplet. Therefore, the diameter of the nozzle 121 is preferably 200 micrometers or less. That is, in the discharging mechanism 10, the diameter of the nozzle 121 is typically in the range of from 10 micrometers through 200 micrometers.

The driving element 13 is formed on the lower surface of the membrane 12. The shape of the driving element 13 can be designed to match the shape of the membrane 12. For example, when the planar shape of the membrane 12 is a circular shape, it is preferable to form a driving element 13 having an annular (ring-like) planar shape around the nozzle 121.

A driving unit 20 can selectively (for example, alternately) apply to the driving element 13, a discharging waveform for vibrating the membrane 12 to form a liquid droplet 310 and a stirring waveform for vibrating the membrane 12 to an extent until which a liquid droplet 310 is not formed.

For example, the discharging waveform and the stirring waveform may both be rectangular waves, and the driving voltage for the stirring waveform may be set lower than the driving voltage for the discharging waveform. This makes it possible for a liquid droplet 310 not to be formed by application of the stirring waveform. That is, it is possible to control the vibration state (degree of vibration) of the membrane 12 depending on whether the driving voltage is high or low.

In the discharging mechanism 10, the driving element 13 is formed on the lower surface of the membrane 12. Therefore, when the membrane 12 is vibrated by means of the driving element 13, a flow can be generated in a direction from the lower portion to the upper portion in the liquid chamber 11.

That is, by applying the discharging waveform to the driving element 13 and controlling the vibration state of the membrane 12, the driving unit 20 can cause the oil 300 retained in the liquid chamber 11 to be discharged through the nozzle 121 in the form of a liquid droplet 310.

In the discharging mechanism 10, bubbles may mix in the oil 300 in the liquid chamber 11. Also in this case, with the atmospherically exposed portion 115 provided at the top of the liquid chamber 11, the discharging mechanism 10 can be evacuated of the bubbles mixed in the oil 300 to the outside air through the atmospherically exposed portion 115. This enables continuous, stable formation of liquid droplets 310 without a need for disposing of a large amount of the liquid for bubble evacuation.

At a timing at which a liquid droplet is not being formed, the membrane 12 may be vibrated to an extent until which a liquid droplet is not formed, in order to positively move the bubbles upward in the liquid chamber 11.

A light source 30 of the counting mechanism is configured to irradiate a flying liquid droplet 310 with light L. A flying state means a state from when the liquid droplet 310 is discharged from the discharging mechanism 10 until when the liquid droplet 310 lands into a container. A flying liquid droplet 310 has an approximately spherical shape at the position at which the liquid droplet 310 is irradiated with the light L. The beam shape of the light L is an approximately circular shape.

It is preferable that the beam diameter of the light L be from about 10 times through 100 times as great as the diameter of the liquid droplet 310. This is for ensuring that the liquid droplet 310 is irradiated with the light L from the light source 30 without fail even when the position of the liquid droplet 310 fluctuates.

However, it is not preferable if the beam diameter of the light L is much greater than 100 times as great as the diameter of the liquid droplet 310. This is because the energy density of the light with which the liquid droplet 310 is irradiated is reduced, to lower the light volume of fluorescence Lf to be emitted in response to the light L serving as excitation light, making it difficult for a light receiving element 60 to detect the fluorescence Lf.

It is preferable that the light L emitted by the light source 30 be pulse light. It is preferable to use, for example, a solid-state laser, a semiconductor laser, and a dye laser. When the light L is pulse light, the pulse width is preferably 10 microseconds or less and more preferably 1 microsecond or less. The energy per unit pulse is preferably roughly 0.1 microjoules or higher and more preferably 1 microjoule or higher, although significantly depending on the optical system such as presence or absence of light condensation.

The fluorescence Lf emitted by the sorted dispersed phase 350 is weaker than the light L emitted by the light source 30. Therefore, a filter configured to attenuate the wavelength range of the light L may be installed at a preceding stage (light receiving surface side) of the light receiving element 60. This enables the light receiving element 60 to obtain an extremely highly contrastive image of the sorted dispersed phase 350. As the filter, for example, a notch filter configured to attenuate a specific wavelength range including the wavelength of the light L may be used.

As described above, it is preferable that the light L emitted by the light source 30 be pulse light. The light L emitted by the light source 30 may be continuously oscillating light. In this case, it is preferable to control the light receiving element 60 to be capable of receiving light at a timing at which a flying liquid droplet 310 is irradiated with the continuously oscillating light, to make the light receiving element 60 receive the fluorescence Lf.

A control unit 70 has a function of controlling the driving unit 20 and the light source 30. The control unit 70 also has a function of obtaining information that is based on the light volume received by the light receiving element 60 and counting the number of sorted dispersed phases 350 contained in the liquid droplet 310 (the case where the number is zero is also included).

As described above, use of the method of the present disclosure for producing a nucleic acid sample-contained container makes it possible to dispense the dispersed phases 350 in a desired number into the capsule 100. Hence, the copy number of the dispersed phase 350, i.e., the intended base sequence to be contained in a container 1 produced as a result of sealing the capsule 100 can be controlled to a known number (a predetermined number).

Figure 9:
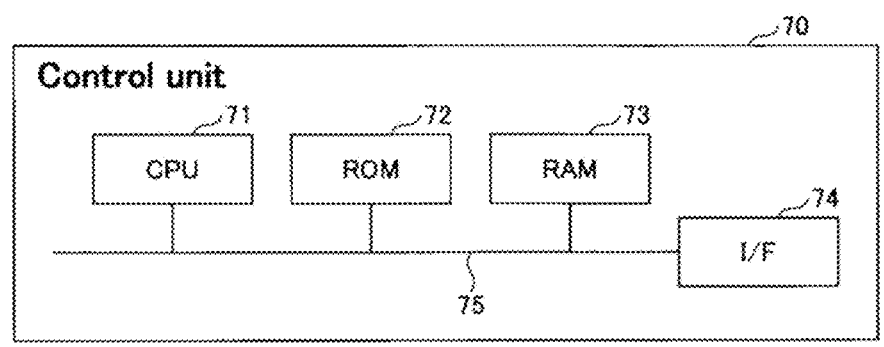
FIG. 9 is a diagram illustrating hardware blocks of a control unit.
Figure 10:
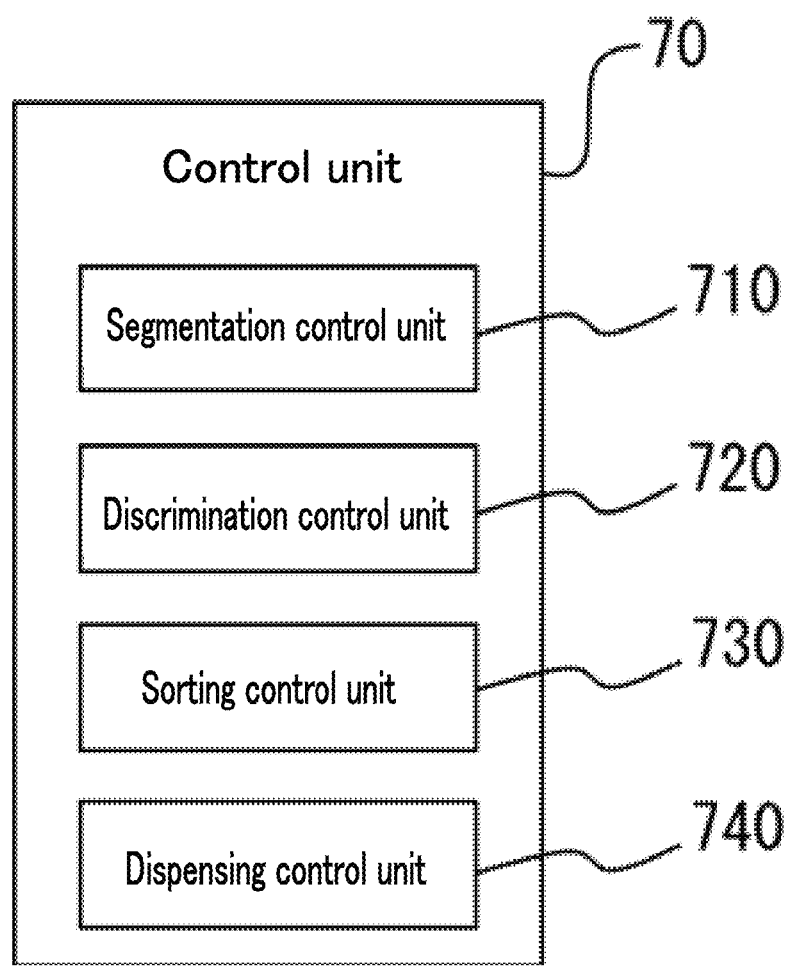
FIG. 10 is a diagram illustrating an example of functional blocks of a control unit.
Figure 11:
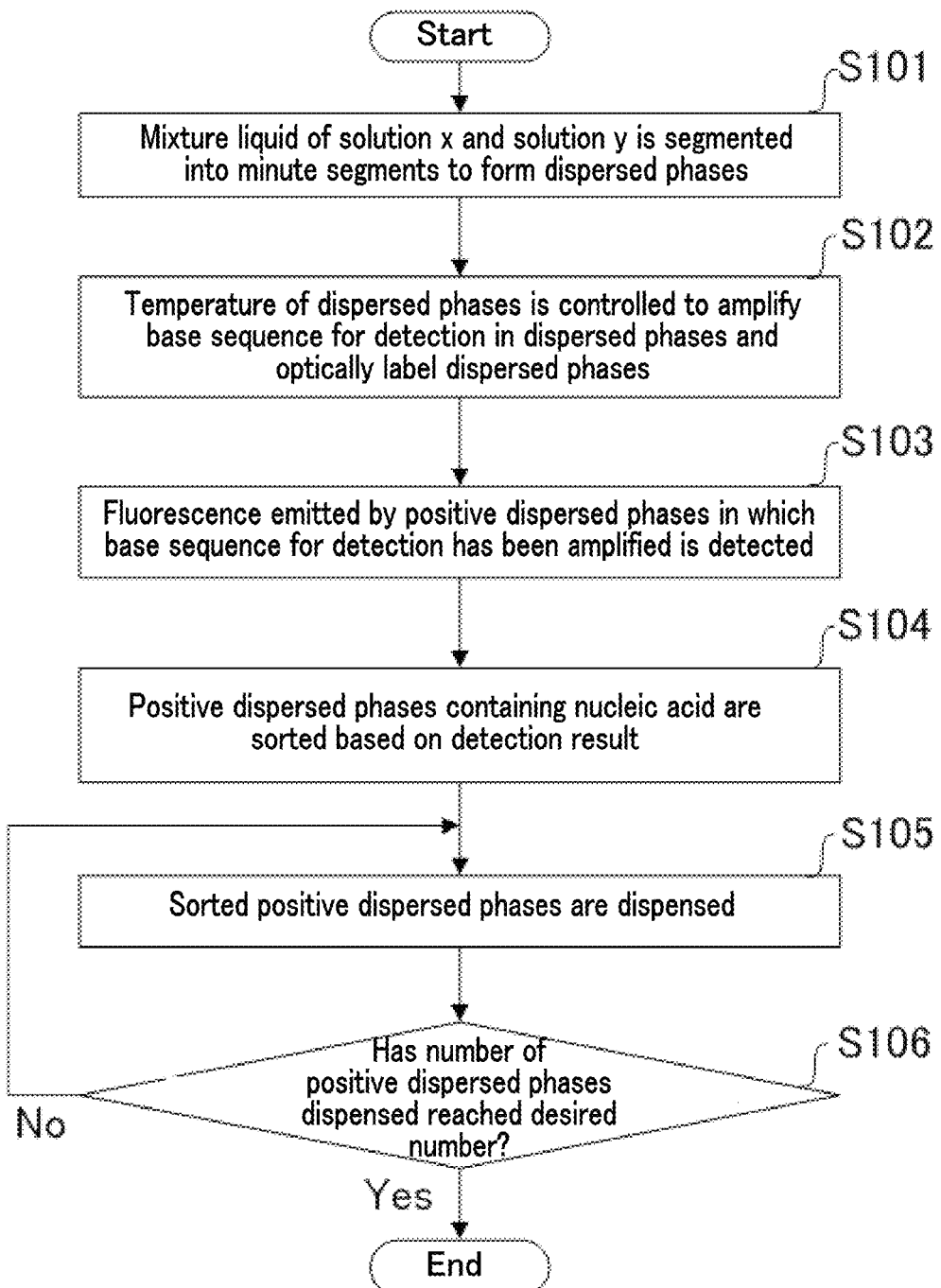
FIG. 11 is a flowchart illustrating an example of a process according to a program for producing a nucleic acid sample-contained container stored in a non-transitory recording medium.

FIG. 9 is a diagram illustrating hardware blocks of the control unit. FIG. 10 is a diagram illustrating functional blocks of the control unit. FIG. 11 is a flowchart illustrating an example of operations of the discharging mechanism and the counting mechanism.

As illustrated in FIG. 9, the control unit 70 includes a CPU 71, a ROM 72, a RAM 73, an I/F 74, and a bus line 75. The CPU 71, the ROM 72, the RAM 73, and the I/F 74 are coupled to one another via the bus line 75.

The CPU 71 is configured to control various functions of the control unit 70. The ROM 72 serving as a memory unit is configured to store programs to be executed by the CPU 71 for controlling the various functions of the control unit 70 and various information. The RAM 73 serving as a memory unit is configured to be used as, for example, the work area of the CPU 71. The RAM 73 is also configured to be capable of storing predetermined information for a temporary period of time. The I/F 74 is an interface configured to couple the discharging mechanism 10 to, for example, another device. The discharging mechanism 10 may be coupled to, for example, an external network via the I/F 74.

As illustrated in FIG. 10, the control unit 70 includes a segmentation control unit 710, a discrimination control unit 720, a sorting control unit 730, and a dispensing control unit 740.

The control unit 70 is configured to control the entire apparatus of the present disclosure configured to produce a nucleic acid sample-contained container.

Next, the control of the control unit 70 when an inkjet type is used as the dispensing unit will be described with reference to FIG. 12 to FIG. 16.

Figure 12:
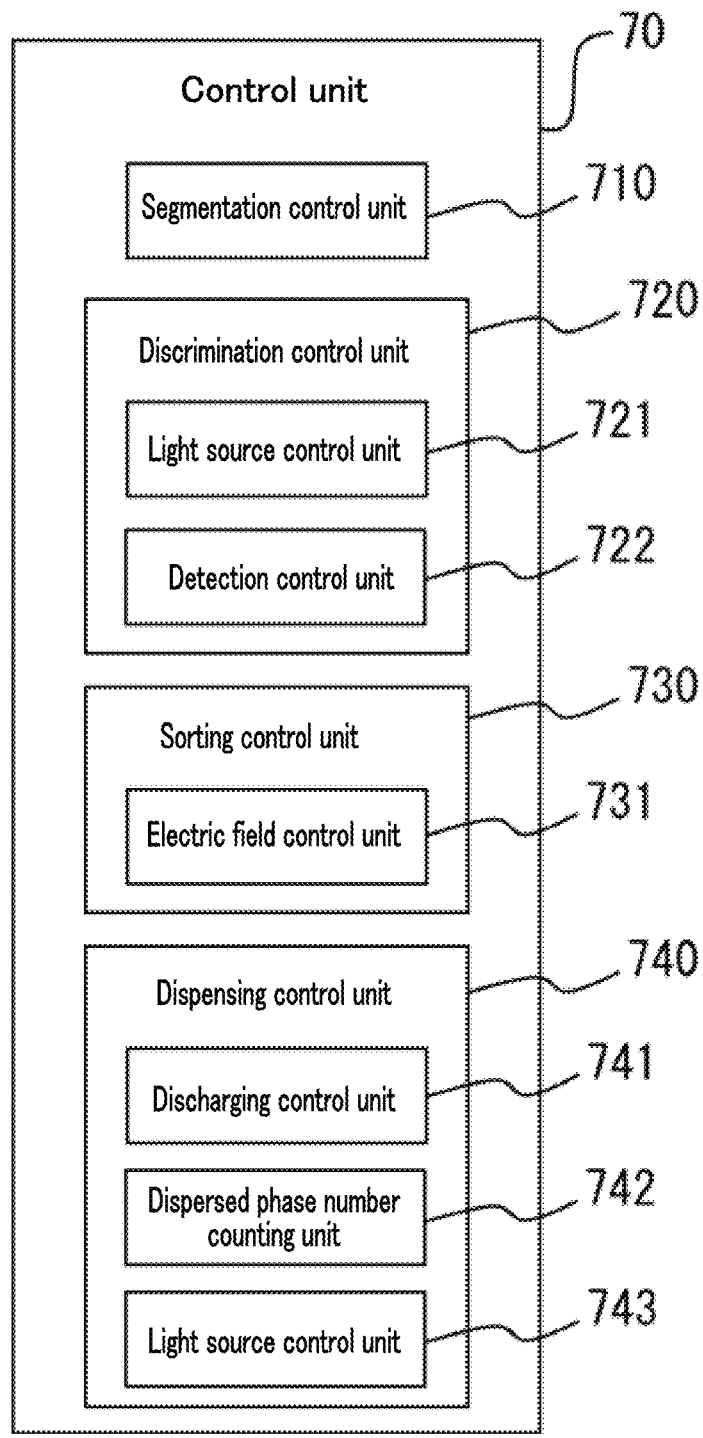
FIG. 12 is a diagram illustrating another example of functional blocks of a control unit.

As illustrated in FIG. 12, the control unit 70 includes the segmentation control unit 710, the discrimination control unit 720, the sorting control unit 730, and the dispensing control unit 740. The sorting control unit 730 includes an electric field control unit 731. The dispensing control unit 740 includes a discharging control unit 741, a dispersed phase number counting unit 742, and a light source control unit 743.

The control unit 70 is configured to control the entire apparatus of the present disclosure configured to produce a nucleic acid sample-contained container.

Figure 13:
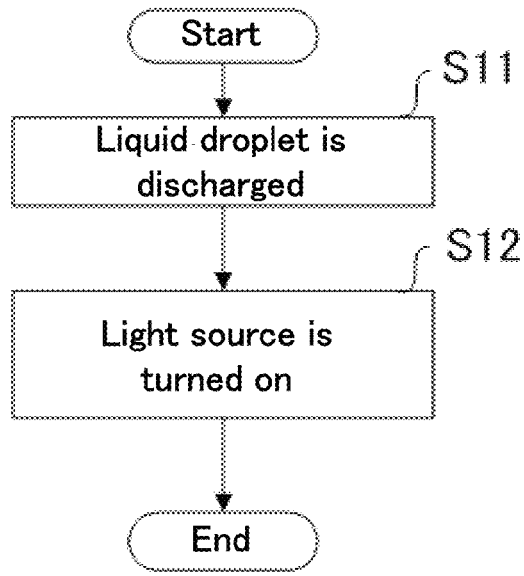
FIG. 13 is a flowchart illustrating an example of an operation of a discharging mechanism of a dispensing unit and a counting mechanism.

With reference to FIG. 12 and FIG. 13, dispersed phase number (particle number) counting by the discharging mechanism 10 will be described. In the step S11, the discharging control unit 741 of the control unit 70 outputs an instruction for discharging to the driving unit 20. Upon reception of the instruction for discharging from the discharging control unit 741, the driving unit 20 supplies a driving signal to the driving element 13 to vibrate the membrane 12. The vibration of the membrane 12 causes a liquid droplet 310 containing a sorted dispersed phase 350 to be discharged through the nozzle 111.

Next, in the step S12, the light source control unit 743 of the control unit 70 outputs an instruction for lighting to the light source 30 in synchronization with the discharging of the liquid droplet 310 (in synchronization with a driving signal supplied by the driving unit 20 to the discharging mechanism 10). In accordance with this instruction, the light source 30 is turned on to irradiate the flying liquid droplet 310 with the light L.

Here, the light is emitted by the light source 30, not in synchronization with discharging of the liquid droplet 310 by the discharging mechanism 10 (supplying of the driving signal to the discharging mechanism 10 by the driving unit 20), but in synchronization with the timing at which the liquid droplet 310 has come flying to a predetermined position in order for the liquid droplet 310 to be irradiated with the light L. That is, the light source control unit 743 controls the light source 30 to emit light at a predetermined period of time of delay from the discharging of the liquid droplet 310 by the discharging mechanism 10 (from the driving signal supplied by the driving unit 20 to the discharging mechanism 10).

For example, the speed v of the liquid droplet 310 to be discharged when the driving signal is supplied to the discharging mechanism 10 may be measured beforehand. Based on the measured speed v, the time t taken from when the liquid droplet 310 is discharged until when the liquid droplet 310 reaches the predetermined position may be calculated, in order that the timing of light irradiation by the light source 30 may be delayed from the timing at which the driving signal is supplied to the discharging mechanism 10 by the period of time of t. This enables a good control on light emission, and can ensure that the liquid droplet 310 is irradiated with the light from the light source 30 without fail.

The dispersed phase number counting unit 742 of the control unit 70 counts the number of sorted dispersed phases 350 contained in the liquid droplet 310 (the case where the number is zero is also included) based on information from the light receiving element 60. The information from the light receiving element 60 indicates the luminance (light volume) and the area value of the sorted dispersed phase 350.

The dispersed phase number counting unit 742 can count the number of sorted dispersed phases 350 by, for example, comparing the light volume received by the light receiving element 60 with a predetermined threshold. In this case, a one-dimensional element may be used or a two-dimensional element may be used as the light receiving element 60.

When a two-dimensional element is used as the light receiving element 60, the dispersed phase number counting unit 742 may use a method of performing image processing for calculating the luminance or the area of the sorted dispersed phase 350 based on a two-dimensional image obtained from the light receiving element 60. In this case, the dispersed phase number counting unit 742 can count the number of sorted dispersed phases 350 by calculating the luminance or the area value of the sorted dispersed phase 350 by image processing and comparing the calculated luminance or area value with a predetermined threshold.

In this way, the driving unit 20 supplies a driving signal to the discharging mechanism 10 retaining the oil 300 suspending sorted dispersed phases 350 to cause the discharging mechanism 10 to discharge a liquid droplet 310 containing the sorted dispersed phase 350, and the flying liquid droplet 310 is irradiated with the light L from the light source 30. Then, the sorted dispersed phase 350 contained in the flying liquid droplet 310 emits the fluorescence Lf in response to the light L serving as excitation light, and the light receiving element 60 receives the fluorescence Lf. Then, the dispersed phase number counting unit 742 counts the number of sorted dispersed phases 350 contained in the flying liquid droplet 310, based on information from the light receiving element 60.

That is, on-the-spot actual observation of the number of sorted dispersed phases 350 contained in the flying liquid droplet 310 is performed. This can realize a better accuracy than hitherto obtained, in counting the number of sorted dispersed phases 350. Moreover, because the sorted dispersed phase 350 contained in the flying liquid droplet 310 is irradiated with the light L and emits the fluorescence Lf that is to be received by the light receiving element 60, an image of the sorted dispersed phase 350 can be obtained with a high contrast, and the frequency of occurrence of erroneous counting of the number of sorted dispersed phases 350 can be reduced.

In the present example, the counting mechanism is configured to count the number of dispersed phases contained in a liquid droplet discharged by the discharging mechanism. However, the counting mechanism is not limited to this configuration. For example, the counting mechanism may be configured to count the number in a flow path through which dispersed phases 512 in which the base sequence for detection B has been amplified and that are sorted by the sorting mechanism 604 flow, or may be configured to count the number in the liquid chamber 11 of the discharging mechanism 10.

Figure 14:
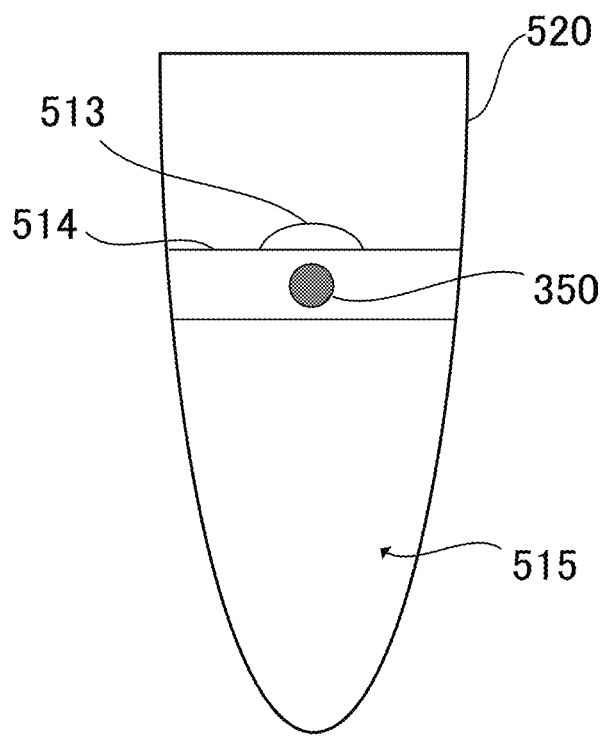
FIG. 14 is a diagram illustrating an example of a state immediately after a dispersed phase containing a nucleic acid including an intended base sequence is dispensed into a container.

FIG. 14 is a diagram illustrating an example of a state immediately after a dispersed phase containing the nucleic acid including the intended base sequence is dispensed into a container.

An aqueous liquid 515 is previously filled in a well 520. In the case where the specific gravity of the oil 300 is lower than the specific gravity of the aqueous liquid 515, immediately after a liquid droplet 310 has landed into the well 520, an oil layer 514 containing a sorted dispersed phase 350, and an oil 513 are positioned on the top of the aqueous liquid 515 as illustrated in FIG. 14.

Figure 15:
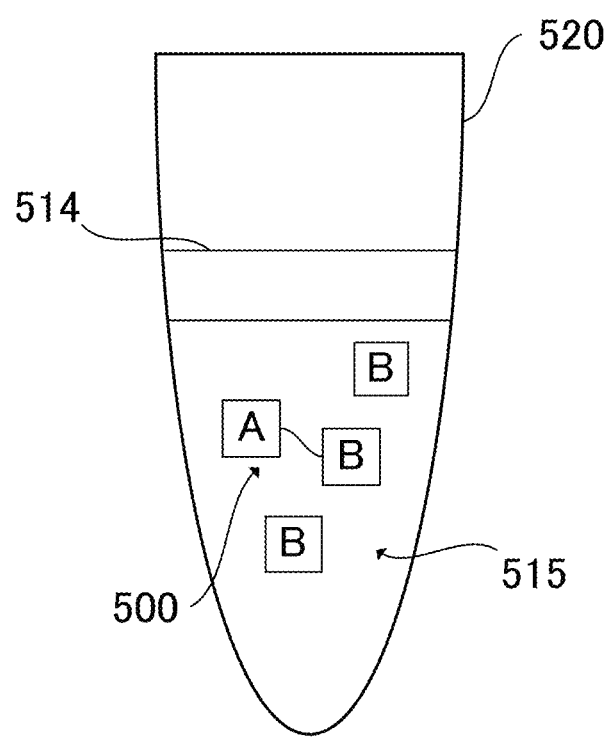
FIG. 15 is a diagram illustrating an example of a state after a dispersed phase containing a nucleic acid including an intended base sequence is dispensed into a container and the dispersed phase is dissolved.

FIG. 15 is a diagram illustrating an example of a state after the dispersed phase containing the nucleic acid including the intended base sequence is dispensed into the container and the dispersed phase is destroyed.

An aqueous component of the sorted dispersed phase 350 contained in the liquid droplet 310 having landed into the well 520 dissolves in a nucleic acid-containing aqueous liquid. Hence, a nucleic acid 500 including the intended base sequence A and amplified base sequences for detection B, contained in the sorted dispersed phase 350, dissolve in the aqueous liquid 515.

In the case where the specific gravity of the oil 300 is higher than the specific gravity of the aqueous liquid 515, the sorted dispersed phase 350 sinks together with the oil 300 to below the aqueous liquid 515, and contacts the interface of the oil 300 and merges with the oil 300, to dissolve in the aqueous liquid 515.

When the sorted dispersed phase 350 has failed to contact the aqueous liquid 515, centrifugation may be performed to form layer separation based on the specific gravities. This enables the sorted dispersed phase 350 to dissolve in the aqueous liquid 515.

Next, the non-transitory recording medium of the present disclosure storing the program for producing a nucleic acid sample-contained container and causing a computer to perform the same functions as the method of the present disclosure for producing a nucleic acid sample-contained container will be described. The process according to the program for producing a nucleic acid sample-contained container stored in the non-transitory recording medium of the present disclosure can be performed using a computer including the control unit 70 constituting the apparatus of the present disclosure configured to produce a nucleic acid sample-contained container.

FIG. 11 is a flowchart illustrating an example of a process according to the program for producing a nucleic acid sample-contained container stored in the non-transitory recording medium.

In the step S101, the control unit 70 causes the dispersed phase forming unit 601 to mix the solution X containing nucleic acids 500 including the intended base sequence A and the base sequence for detection B different from the intended base sequence with the solution Y containing the nucleic acid amplifying reagent and the fluorescent labeling reagent and segment the mixture liquid of the solution X and the solution Y into minute segments to form dispersed phases, and then moves the flow to the step S102.

In the step S102, the control unit 70 causes the amplifying unit 602 to raise and drop the temperature of dispersed phases 510 containing the nucleic acid 500, the nucleic acid amplifying reagent, and the fluorescent labeling reagent between a plurality of temperature ranges while the dispersed phases 510 are flowing through a meandering flow path, and then moves the flow to the step S103. By the temperature of the dispersed phases 510 being raised and dropped to temperatures in the plurality of temperature ranges, the base sequence for detection B is amplified, to bring dispersed phases 512 into an optically labeled state.

In the step S103, the control unit 70 causes the discriminating unit 603 to detect fluorescence emitted by the positive dispersed phases 512 in which the base sequence for detection B has been amplified, and then moves the flow to the step S104.

In the step S104, the control unit 70 causes the sorting mechanism 604 to dielectrophoretically sort the positive dispersed phases 512 in which the base sequence for detection B has been amplified based on the detection result of the discriminating unit 603, and then moves the flow to the step S105. Here, sorting the positive dispersed phases 512 in which the base sequence for detection B has been amplified means conveying only the positive dispersed phases 512 in which the base sequence for detection B has been amplified to the discharging mechanism 10 by the sorting mechanism 604 based on the intensity of the light signal from the dispersed phases detected in the step S103.

In the step S105, the control unit 70 causes the discharging mechanism 10 to dispense the positive dispersed phases 512 in which the base sequence for detection B has been amplified into a capsule 100, and then moves the flow to the step S106.

In the step S106, the control unit 70 causes the light source 30 and the light receiving element 60 to detect the positive dispersed phases 512 dispensed, and returns the flow to the step S105 when the number of positive dispersed phases 512 detected has not reached a desired number set by the user (for example, the number of dispersed phases to be dispensed into a capsule 520). On the other hand, the control unit 70 terminates the flow when the counted number has reached the desired number set by the user.

By repeating the process illustrated in FIG. 11 a plurality of times, it is possible to dispense the nucleic acids into a plurality of capsules 520.

Figure 16:
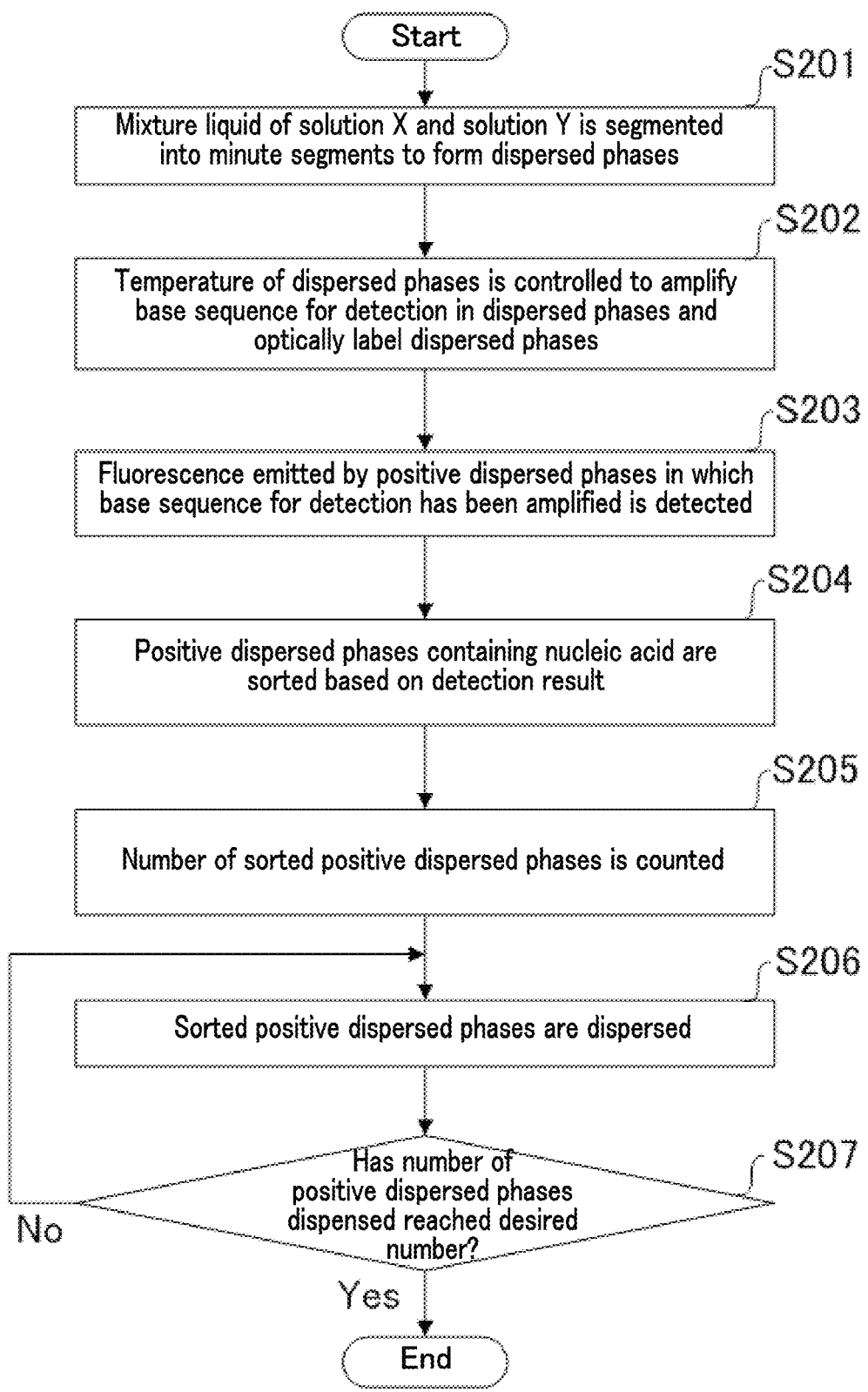
FIG. 16 is a flowchart illustrating another example of a process according to a program for producing a nucleic acid sample-contained container stored in a non-transitory recording medium.

FIG. 16 is a flowchart illustrating another example of the process according to the program for producing a nucleic acid sample-contained container stored in the non-transitory recording medium.

In FIG. 16, the step S201 is the same process as S101, the step S202 is the same process as S102, the step S203 is the same process as S103, the step S204 is the same process as S104, and the step S206 is the same process as S105. Therefore, descriptions about these steps will be skipped.

In the step S205, the control unit 70 causes the light source 30 and the light receiving element 60 to count the number of positive dispersed phases sorted in the step S204 in the flow path, and then moves the flow to the step S206.

In the step S207, the control unit 70 determines whether the number of positive dispersed phases 512 dispensed in the step S206 has reached a desired number set by the user (for example, the number of dispersed phases to be dispensed into the well 520), based on the number of positive dispersed phases 512 counted in the step S205. When it is determined that the number of positive dispersed phases 512 dispensed has not reached the desired number set by the user, the control unit 70 returns the flow to the step S206. On the other hand, when it is determined that the number of positive dispersed phases 512 dispensed has reached the desired number set by the user, the control unit 70 terminates the flow.

By repeating the process illustrated in FIG. 16 a plurality of times, it is possible to dispense the nucleic acids into a plurality of wells 520.

(Nucleic Acid Sample)

The nucleic acid sample of the present disclosure includes a first nucleic acid molecule including a base sequence for detection and a base sequence different from the base sequence for detection, and a second nucleic acid molecule including the base sequence for detection. The nucleic acid sample includes the first nucleic acid molecule in a predetermined number. The nucleic acid sample further includes other members as needed.

The form of the nucleic acid sample of the present disclosure is not particularly limited. Examples of the form of the nucleic acid sample include a dispersed phase. Description about the dispersed phase will be skipped because the dispersed phase is the same as the dispersed phase described in the description of the nucleic acid sample-contained container of the present disclosure.

EXAMPLES

The present disclosure will be described below by way of Examples. However, the present disclosure should not be construed as being limited to these Examples.

Example 1

<Production of Nucleic Acid (dsDNA) Sample-Contained Container (Particulate Container)>

—Preparation of Mixture Liquid of Nucleic Acid, Nucleic Acid Amplifying Reagent, and Fluorescent Labeling Reagent—

A reagent was prepared at a mixing ratio presented in Table 2, using DNA600-G (available from National Institute of Advanced Industrial Science and Technology, NMIJ CRM 6205-a, see SEQ ID NO. 1) as a template nucleic acid, a forward primer (see SEQ ID NO. 2) and a reverse primer (see SEQ ID NO. 3) complementary with the nucleic acid as nucleic acid amplifying reagents, a base sequence complementary with a part of the nucleic acid between the forward primer and the reverse primer as a fluorescent labeling reagent, FAM as a fluorescent dye, a TaqMan probe (see SEQ ID NO. 4) including TAMRA as a quencher, SUPERMIX (available from Bio-Rad Laboratories, K.K., DDPCR SUPERMIX FOR PROBES (no dUTP), 186-3025), and NFW (available from Thermo Fisher Scientific Inc., ULTRAPURE DNASE/RNASE-FREE-DISTILLED WATER, 10977-015). Finally, the prepared reagent was filled into plates for digital PCR (available from Bio-Rad Laboratories, K.K., DDPCR96-WELL PLATES, 12001925) in an amount of 22 microliters each. Each reagent was used at the concentration diluted with NWF as presented in Table 2.

TABLE 2

| Composition | Ratio | Liquid amount (microliter) |
| --- | --- | --- |
| DDPCR SUPERMIX FOR PROBES (no dUTP) | 11 | 93.50 |
| Forward primer (10 micromoles/L) | 0.3 | 2.55 |
| Reverse primer (10 micromoles/L) | 0.3 | 2.55 |
| TaqMan Probe (5 micromoles/L) | 0.2 | 1.70 |
| Template (DNA600-G) (1.5 fmol/L) | 2.5 | 21.25 |
| NFW | 7.7 | 65.45 |
| Total | 22 | 187 |

—Step of Forming Dispersed Phases—

The prepared mixture liquid was segmented into dispersed phases, using a droplet generator (available from Bio-Rad Laboratories, K.K., apparatus name: AUTOMATED DROPLET GENERATOR). AUTOMATED DROPLET GENERATOR OIL FOR PROBES available from Bio-Rad Laboratories, K.K. was used as the solvent of the mobile phase. The produced droplet suspension was aluminum-sealed using a plate sealer (available from Bio-Rad Laboratories, K.K., product name: PX1 PLATE SEALER), and then immediately subjected to the next amplifying step.

—Amplifying Step—

The amplifying step was performed according to the thermal cycling process presented in Table 3, using a thermal cycler (available from Bio-Rad Laboratories, K.K., apparatus name: T100 THERMAL CYCLER).

TABLE 3

| Cycling Step | Temperature | Time | Number of Cycles | Ramp Rate |
| --- | --- | --- | --- | --- |
| Enzyme activation | 95 degrees C. | 10 min | 1 | 2 degrees C./sec |
| Denaturation | 94 degrees C. | 30 sec | 40 | |
| Annealing/ extension | 55 degrees C. | 1 min | | |
| Enzyme deactivation | 98 degrees C. | 10 min | 1 | |
| Hold | 4 degrees C. | Infinite | 1 | |

—Confirmation of Nucleic Acid Amplification and Calculation of Uncertainty—

Figure 17:
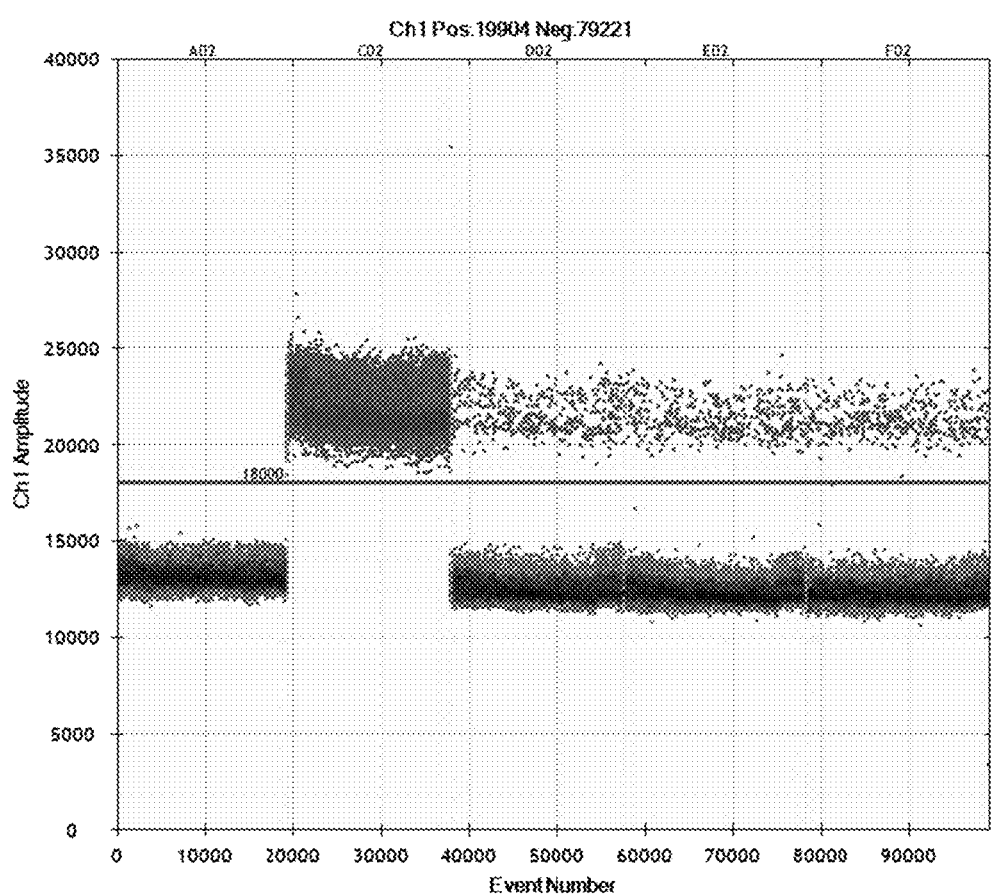
FIG. 17 is a graph plotting an example of a result related with production of a nucleic acid sample-contained container of the present disclosure.

Confirmation of fluorescence from dispersed phases in which nucleic acid amplification occurred (may also be referred to as positive dispersed phases) was performed using a droplet reader (available from Bio-Rad Laboratories, K.K., apparatus name: QX200 DROPLET READER), and based on the detection result (FIG. 17 and Table 4), the probability at which the intended base sequence was contained in each copy number in these dispersed phases was calculated according to a calculation process (Formula 1) taking a Poisson distribution into account. The calculation results (in the "D02" case indicated in Table 4) are presented in Table 5.

TABLE 4

| Well | Number of positive dispersed phases (phase) | Number of negative dispersed phases (phase) | Nucleic acid concentration in solution (copy number/ microliter) |
|---|---|---|---|
| A02 | 1 | 19,481 | 0 |
| C02 | 18,617 | 0 | 1,000,000 |
| D02 | 450 | 19,087 | 27.4 |
| E02 | 429 | 20,367 | 24.5 |
| F02 | 407 | 20,286 | 23.4 |

TABLE 5

| | Copy number contained per droplet of positive dispersed phase | | | | |
|---|---|---|---|---|---|
| | 1 (copy) | 2 (copy) | 3 (copy) | 4 (copy) | 5 (copy) |
| Probability (%) at which intended base sequence was contained in each copy number per droplet of dispersed phase | 98.85 | 1.14 | 0.01 | 0.00 | 0.00 |

—Steps of Discriminating and Sorting Dispersed Phases—

Figure 18:
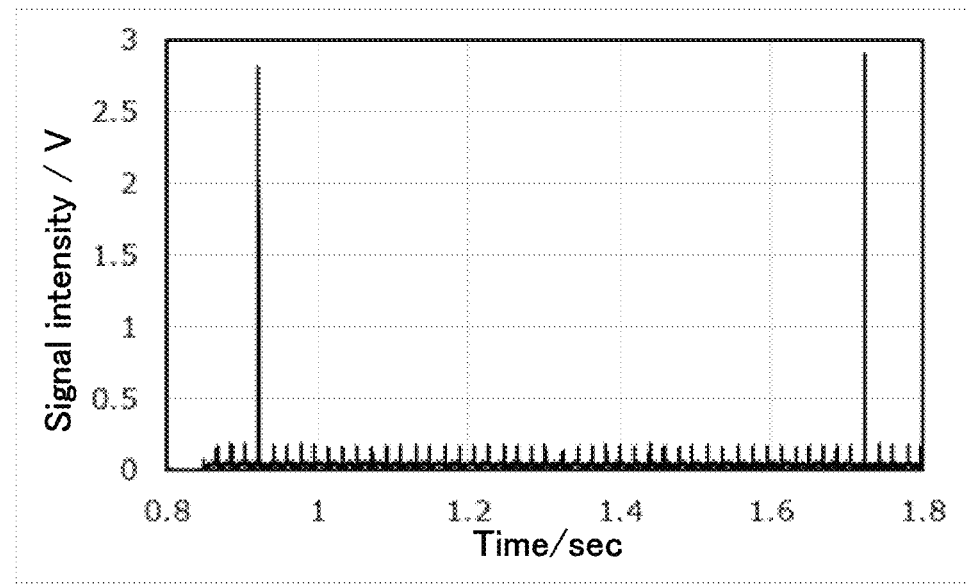
FIG. 18 is a graph plotting another example of a result related with production of a nucleic acid sample-contained container of the present disclosure.
Figure 19:
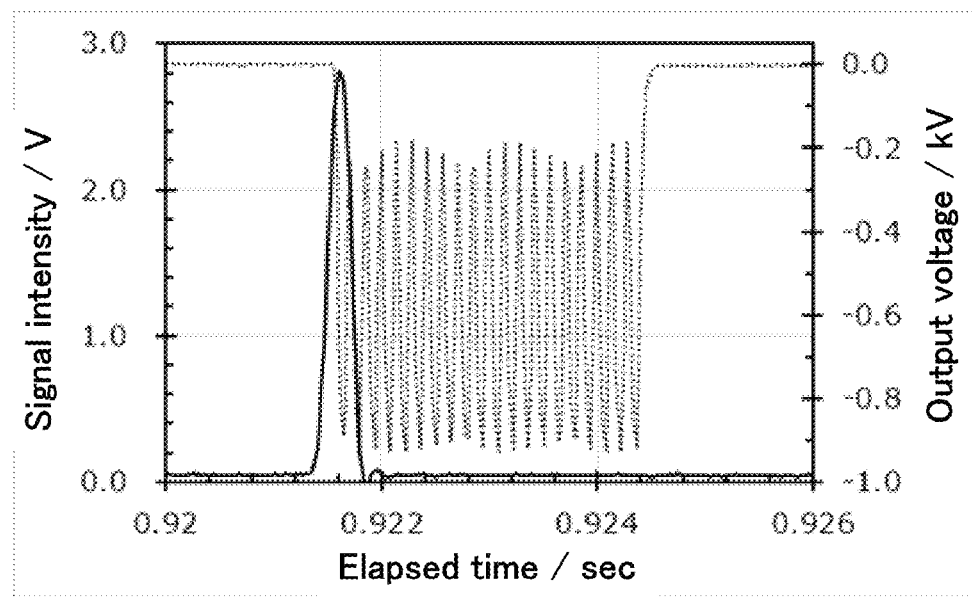
FIG. 19 is a graph plotting an example of an operation of a sorting unit involved in production of a nucleic acid sample-contained container of the present disclosure.
Figure 20:
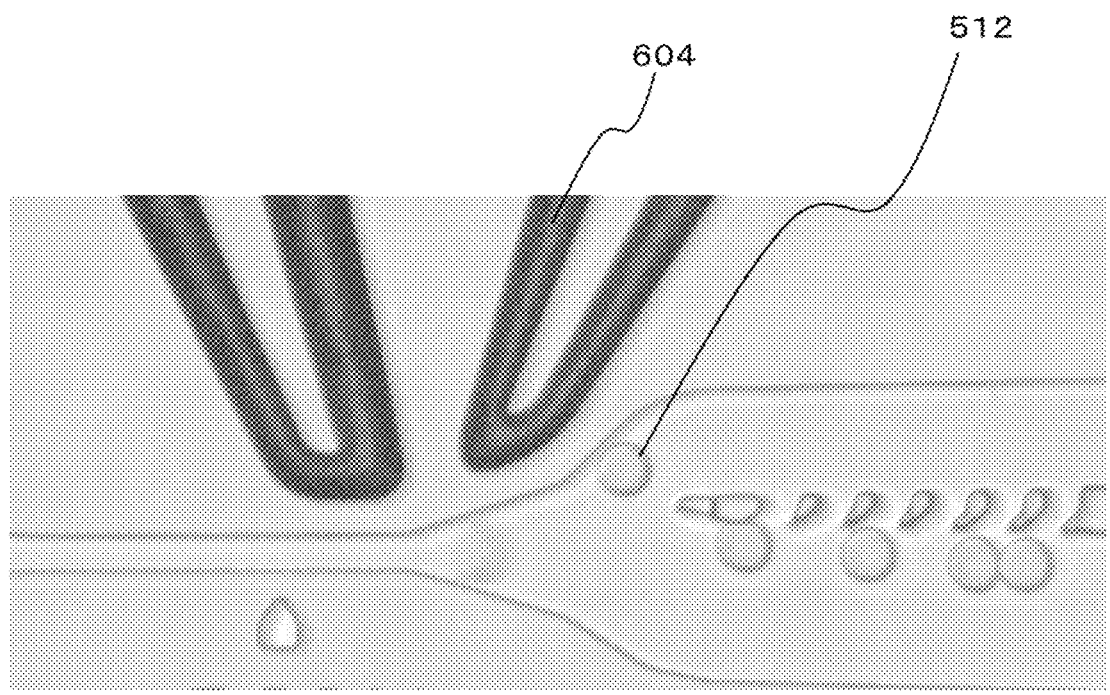
FIG. 20 is a view illustrating an operation of a sorting unit involved in production of a nucleic acid sample-contained container of the present disclosure.

In sorting of the dispersed phases in which nucleic acid amplification occurred (positive dispersed phases) and dispensing of the dispersed phases into a particulate container, discriminating/sorting was performed using, for example, the sorting mechanism 604 illustrated in FIG. 6. Positive dispersed phase detection results are presented in FIG. 18. An application waveform (dotted line) was applied in order to generate a non-uniform electric field for the positive dispersed phases (solid line) (FIG. 19). FIG. 20 illustrates how the positive dispersed phases 512 were sorted. The sorted positive dispersed phases were introduced into the discharging mechanism in the next dispensing step.

—Step of Dispensing Dispersed Phases—

Then, a flow path configured to dispense the dispersed phases into a particulate container as illustrated in FIG. 7 was provided, to dispense the sorted dispersed phases while detecting the number of dispersed phases. As the capsule used as the particulate container, MP CAPSULE NO. 5 (available from As One Corporation) was used. The capsule into which the dispersed phases were dispensed was colored as visually recognizable indication of information on the total copy number of the intended base sequence in the particulate container obtained from the calculated copy number of the intended base sequence contained per droplet of a dispersed phase and uncertainty of the DNA copy number.

Example 2

<Production of Nucleic Acid (dsDNA) Sample-Contained Container>

Dispersed phases were dispensed into a container in the same manner as in Example 1. As the container, MICRO-AMP™ OPTICAL 96-WELL REACTION PLATE WITH BARCODE (available from Thermo Fisher Scientific Inc.) was used.

After the positive dispersed phases were dispensed into the container, the container was subjected to vacuum drying. A barcode was applied on the side surface of the dried container (plate). By the barcode, it would be possible to confirm a calculation result of the total copy number of the intended base sequence dispensed into the container (calculated from the copy number of the intended base sequence contained per droplet of a dispersed phase) and information on copy number uncertainty counting the number of both of sense strands and antisense strands of dsDNA dispensed into the container.

Example 3

<Production of RNA Sample-Contained Container>
—Preparation of RNA-DNA Hybridized Nucleic Acid Solution—

RNA500-A (available from National Institute of Advanced Industrial Science and Technology, NMIJ CRM 6204-a, see SEQ ID NO. 5) as a template nucleic acid and ssDNA (single-strand DNA) (see SEQ ID NO. 6) were mixed according to the composition presented in Table 6, subsequently thermally denatured at 95 degrees C. for 2 minutes, and cooled for 1 hour to normal temperature, to be hybridized sufficiently, to synthesize RNA-DNA double strands. Subsequently, EXONUCLEASE I (available from Takara Bio Inc.) (5 microliters) was added to the resultant, and left to stand still at normal temperature for 30 minutes, to remove single-strand DNA. Subsequently, the resultant was subjected to deactivation treatment at 80 degrees C. for 15 minutes to deactivate EXONUCLEASE I, to obtain an RNA-DNA hybridized nucleic acid solution.

TABLE 6

| Composition | Ratio | Liquid amount (microliter) |
|---|---|---|
| RNA500-A (1 micromole/L) | 1.0 | 50 |
| ssDNA (1 micromole/L) | 2.0 | 100 |
| EXONUCLEASE I (5 U/microliter) | 0.1 | 5 |

Figure 21:
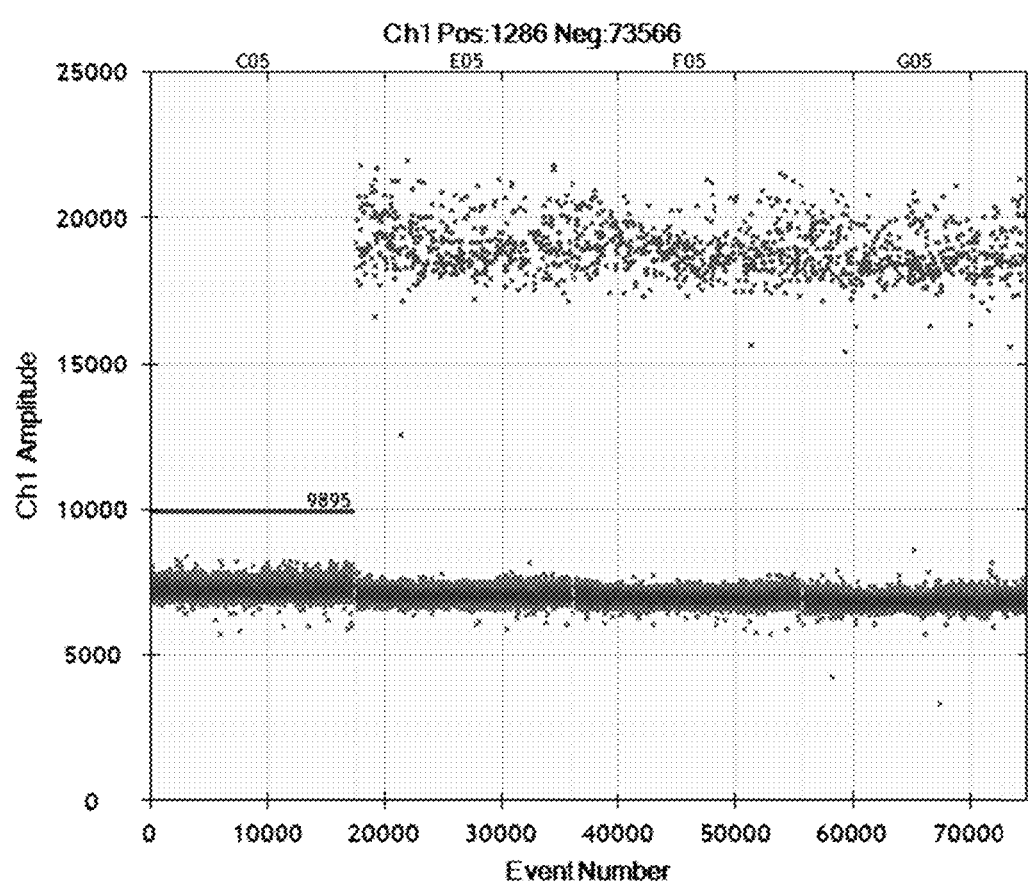
FIG. 21 is a graph plotting an example of a result related with production of a nucleic acid sample-contained container of the present disclosure.

Preparation of a mixture liquid of a nucleic acid, nucleic acid amplifying reagents, and a fluorescent labeling reagent, formation of dispersed phases, the amplifying step, and confirmation of nucleic acid amplification and calculation of uncertainty were performed in the same manner as in Example 1, except that the RNA-DNA hybridized solution was used as a template nucleic acid, a forward primer (see SEQ ID NO. 7) and a reverse primer (see SEQ ID NO. 8) complementary with the nucleic acid were used as nucleic acid amplifying reagents, a base sequence complementary with a part of the nucleic acid between the forward primer and the reverse primer was used as a fluorescent labeling reagent, FAM was used as a fluorescent dye, and a TaqMan probe (see SEQ ID NO. 9) including TAMRA was used as a quencher. The composition is presented in Table 7 below. The results are presented in FIG. 18, FIG. 21, Table 8, and Table 9 (in the "F05" case indicated in Table 8).

TABLE 7

| Composition | Ratio | Liquid amount (microliter) |
|---|---|---|
| DDPCR SUPERMIX FOR PROBES (no dUTP) | 11 | 93.50 |
| Forward primer (10 micromoles/L) | 0.3 | 2.55 |
| Reverse primer (10 micromoles/L) | 0.3 | 2.55 |
| TaqMan Probe (5 micromoles/L) | 0.2 | 1.70 |
| RNA-DNA hybridized solution (1.5 fM) | 2.5 | 21.25 |
| NFW | 7.7 | 65.45 |
| Total | 22 | 187 |

TABLE 8

| Well | Number of positive dispersed phases (phase) | Number of negative dispersed phases (phase) | Nucleic acid concentration in solution (copy number/ microliter) |
|---|---|---|---|
| C05 | 0 | 17,634 | 0 |
| E05 | 412 | 18,693 | 26.2 |
| F05 | 440 | 19,484 | 26.9 |
| G05 | 434 | 19,401 | 27 |

TABLE 9

| | Copy number contained per droplet of positive dispersed phase | | | | |
|---|---|---|---|---|---|
| | 1 (copy) | 2 (copy) | 3 (copy) | 4 (copy) | 5 (copy) |
| Probability (%) at which intended base sequence was contained in each copy number per droplet of dispersed phase | 98.90 | 1.09 | 0.01 | 0.00 | 0.00 |

—Step of Discriminating/Sorting Dispersed Phases—

The dispersed phases obtained were discriminated and sorted in the same manner as in Example 1.

—Step of Dispensing Dispersed Phases—

The sorted dispersed phases were dispensed into a container in the same manner as in Example 2. As the container, MICROAMP™ OPTICAL 96-WELL REACTION PLATE WITH BARCODE (Thermo Fisher Scientific Inc.) was used. After positive dispersed phases were dispensed into the container (plate), the container was subjected to vacuum drying. A barcode was applied on the side surface of the dried container (plate). By the barcode, it would be possible to confirm a calculation result of the total copy number of the intended base sequence dispensed into the container (plate) (calculated from the copy number of the intended base sequence contained per droplet of a dispersed phase) and information on uncertainty of the copy number of RNA dispensed into the container.

Example 4

<Production of Nucleic Acid (ssDNA) Sample Contained-Container>

—Preparation of Mixture Liquid of Nucleic Acid, Nucleic Acid Amplifying Reagent, and Fluorescent Labeling Reagent—

Figure 22:
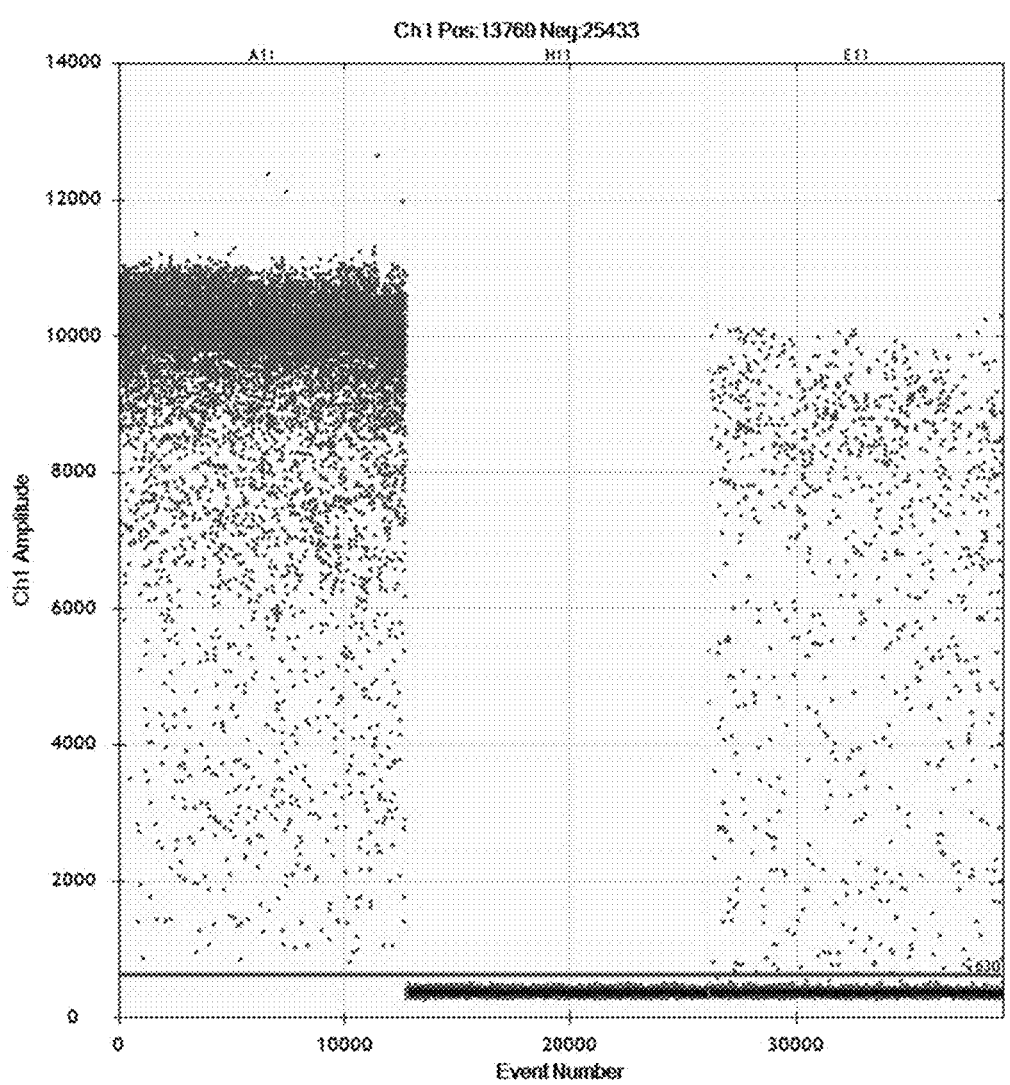
FIG. 22 is a graph plotting another example of a result related with production of a nucleic acid sample-contained container of the present disclosure.

Preparation of a mixture liquid of a nucleic acid, nucleic acid amplifying reagents, and a fluorescent labeling reagent, formation of dispersed phases, the amplifying step, and confirmation of nucleic acid amplification and calculation of uncertainty were performed in the same manner as in Example 1, except that k03_ssDNA (available from Integrated DNA Technologies, Inc., see SEQ ID NO. 10) was used as a template nucleic acid, a forward primer (see SEQ ID NO. 11) and a reverse primer (see SEQ ID NO. 12) complementary with the nucleic acid were used as nucleic acid amplifying reagents, a base sequence complementary with a part of the nucleic acid between the forward primer and the reverse primer was used as a fluorescent labeling reagent, FAM was used as a fluorescent dye, and a TaqMan probe (see SEQ ID NO. 13) including ZEN and TAMRA was used as a quencher. The composition is presented in Table 10 below. A thermal cycling process in the amplifying step is presented in Table 11. The results are presented in FIG. 22, Table 12, and Table 13 (in the "E11" case indicated in Table 12).

TABLE 10

| Composition | Ratio | Liquid amount (microliter) |
|---|---|---|
| DDPCR SUPERMIX FOR PROBES (no dUTP) | 11 | 93.50 |
| Forward primer (20 micromoles/L) | 1 | 8.50 |
| Reverse primer (20 micromoles/L) | 1 | 8.50 |
| TaqMan Probe (10 micromoles/L) | 0.6 | 5.10 |
| Template (k03_ssDNA) (1.5 fmol/L) | 2.2 | 18.70 |
| NFW | 6.2 | 52.70 |
| Total | 22 | 187 |

TABLE 11

| Cycling Step | Temperature | Time | Number of Cycles | Ramp Rate |
|---|---|---|---|---|
| Enzyme activation | 95 degrees C. | 10 min | 1 | 2 degrees C./sec |
| Denaturation | 94 degrees C. | 30 sec | 40 | |
| Annealing/ extension | 53 degrees C. | 1 min | | |
| Enzyme deactivation | 98 degrees C. | 10 min | 1 | |
| Hold | 4 degrees C. | Infinite | 1 | |

TABLE 12

| Well | Number of positive dispersed phases (phase) | Number of negative dispersed phases (phase) | Nucleic acid concentration in solution (copy number/ microliter) |
|---|---|---|---|
| A11 | 12,768 | 0 | 1,000,000 |
| H11 | 0 | 13,461 | 0.0 |
| E11 | 1,001 | 11,972 | 94.0 |

TABLE 13

| | Copy number contained per droplet of positive dispersed phase | | | | |
|---|---|---|---|---|---|
| | 1 | 2 | 3 | 4 | 5 |
| Probability (%) at which intended base sequence was contained in each copy number per droplet of dispersed phase | 96.19% | 3.71% | 0.10% | 0.00% | 0.00% |

—Step of Discriminating/Sorting Dispersed Phases—

The dispersed phases obtained were discriminated and sorted in the same manner as in Example 1.

—Step of Dispensing Dispersed Phases—

The sorted dispersed phases were dispensed into a container in the same manner as in Example 2. As the container, MICROAMP™ OPTICAL 96-WELL REACTION PLATE WITH BARCODE (available from Thermo Fisher Scientific Inc.) was used. After positive dispersed phases were dispensed into the container (plate), the container was subjected to vacuum drying. A barcode was applied on the side surface of the dried container (plate). By the barcode, it would be possible to confirm a calculation result of the total copy number of the intended base sequence dispensed into the container (plate) (calculated from the copy number of the intended base sequence contained per droplet of a dispersed phase) and information on uncertainty of the copy number of ssDNA dispensed into the container.

Aspects of the present disclosure were as follows, for example.

<1> A nucleic acid sample-contained container including:
a first nucleic acid molecule including an intended base sequence and a base sequence for detection different from the intended base sequence; and
a second nucleic acid molecule free of the intended base sequence but including the base sequence for detection, wherein the nucleic acid sample-contained container includes the first nucleic acid molecule in a predetermined number.

<2> The nucleic acid sample-contained container according to <1>, wherein the first nucleic acid molecule includes the intended base sequence in a plural number in a same molecule.

<3> The nucleic acid sample-contained container according to <2>, wherein when the first nucleic acid molecule includes the intended base sequence in the plural number, the first nucleic acid molecule includes at least one artificial nucleic acid base unamplifiable by a natural nucleic acid synthetase between one intended base sequence and another intended base sequence.

<4> The nucleic acid sample-contained container according to any one of <1> to <3>, wherein a number in which the intended base sequence is included is less than 1,000, and a coefficient of variation (CV value) for the number in which the intended base sequence is included is lower than 20%.

<5> The nucleic acid sample-contained container according to any one of <1> to <4>, wherein the nucleic acid molecules are artificially synthesized nucleic acid molecules.

<6> The nucleic acid sample-contained container according to any one of <1> to <5>, including a shell encapsulating the first nucleic acid molecule and the second nucleic acid molecule.

<7> The nucleic acid sample-contained container according to any one of <1> to <5>, wherein the nucleic acid sample-contained container is either a solid particle including the first nucleic acid molecule and the second nucleic acid molecule or a gel particle including the first nucleic acid molecule and the second nucleic acid molecule.

<8> The nucleic acid sample-contained container according to <6> or <7>,
wherein the nucleic acid sample-contained container is soluble.

<9> The nucleic acid sample-contained container according to any one of <1> to <8>,
wherein the nucleic acid sample-contained container is colored.

<10> A nucleic acid sample-contained container including:
a dispersed phase containing a nucleic acid;
a continuous phase; and
a protective member encapsulating the dispersed phase and the continuous phase.

<11> The nucleic acid sample-contained container according to any one of <1> to <10>,
wherein the first nucleic acid molecule is a single-strand nucleic acid molecule.

<12> The nucleic acid sample-contained container according to any one of <1> to <11>,
wherein the first nucleic acid molecule includes the base sequence for detection at a 5' terminal side of the intended base sequence.

<13> A method for producing a nucleic acid sample-contained container, the method including:
forming a plurality of dispersed phases containing a nucleic acid including: an intended base sequence; and a base sequence for detection different from the intended base sequence;
amplifying the base sequence for detection in the dispersed phases;
discriminating the dispersed phases in which the base sequence for detection has been amplified; and
dispensing the dispersed phases discriminated in the discriminating as containing the nucleic acid in which the base sequence for detection has been amplified.

<14> The method for producing a nucleic acid sample-contained container according to <13>,
wherein a probability at which each of the dispersed phases contains one intended base sequence is 90% or higher.

<15> The method for producing a nucleic acid sample-contained container according to <13> or <14>,
wherein the discriminating includes detecting a light signal emitted by the dispersed phases and discriminating the dispersed phases containing the nucleic acid in which the base sequence for detection has been amplified.

<16> The method for producing a nucleic acid sample-contained container according to any one of <13> to <15>,
wherein the dispensing includes dispensing the dispersed phases containing the nucleic acid including the intended base sequence in a number specified in the discriminating.

<17> The method for producing a nucleic acid sample-contained container according to any one of <13> to <16>,
wherein the forming is performed with a nucleic acid-containing liquid containing the nucleic acid at a concentration at which the nucleic acid is contained in at most one molecule in each one of the dispersed phases.

<18> The method for producing a nucleic acid sample-contained container according to any one of <12> to <15>,
wherein the dispensing is performed by an inkjet method.

<19> The method for producing a nucleic acid sample-contained container according to any one of <13> to <18>,
wherein the dispensing is performed while counting a number in which the dispersed phases are contained in a liquid droplet discharged.

<20> The method for producing a nucleic acid sample-contained container according to any one of <13> to <19>,
wherein the dispensing is performed with previous counting, before the dispensing, of a number in which the dispersed phases discriminated are present.

<21> An apparatus configured to produce a nucleic acid sample-contained container, the apparatus including:
a dispersed phase forming unit configured to form a plurality of dispersed phases containing a nucleic acid including an intended base sequence and a base sequence for detection different from the intended base sequence;
an amplifying unit configured to amplify the base sequence for detection in the dispersed phases;
a discriminating unit configured to discriminate the dispersed phases in which the base sequence for detection has been amplified; and
a dispensing unit configured to dispense the dispersed phases discriminated by the discriminating unit as containing the nucleic acid in which the base sequence for detection has been amplified.

<22> A non-transitory recording medium storing a program for producing a nucleic acid sample-contained container and causing a computer to execute a process including:
forming a plurality of dispersed phases containing a nucleic acid including an intended base sequence and a base sequence for detection different from the intended base sequence;
amplifying the base sequence for detection in the dispersed phases; discriminating the dispersed phases in which the base sequence for detection has been amplified; and dispensing the dispersed phases discriminated in the discriminating as containing the nucleic acid in which the base sequence for detection has been amplified.
<23> A nucleic acid sample including;
a first nucleic acid molecule including a base sequence for detection and a base sequence different from the base sequence for detection; and a second nucleic acid molecule including the base sequence for detection, wherein the nucleic acid sample includes the first nucleic acid molecule in a predetermined number.

The nucleic acid sample-contained container according to any one of <1> to <12>, the method for producing a nucleic acid sample-contained container according to any one of <13> to <20>, the apparatus configured to produce a nucleic acid sample-contained container according to <21>, the non-transitory recording medium storing a program for producing a nucleic acid sample-contained container according to <22>, and the nucleic acid sample according to <23> can solve the various problems in the related art and can achieve the object of the present disclosure.

What is claimed is:

1. A nucleic, acid sample-contained container, comprising:
a plurality of shapes selected from the group consisting of a concave bottom and a section on a substrate, wherein each of the plurality of shapes comprises a droplet consisting of:
a solution, wherein the solution is selected from the group consisting of water, nuclease-free water, a broth, a separation liquid, a diluted solution, a buffer, an organic substance lysing liquid, an organic solvent, an electrolyte aqueous solution, an inorganic salt aqueous solution, a metal aqueous solution, a labeling agent or reagent, and a mixture liquid of these solutions;
a nucleic acid amplifying agent and a fluorescent labeling reagent; and
at least one of a first nucleic acid molecule and a plurality of a second nucleic acid molecule, wherein the at least one of the first nucleic acid molecule and the plurality of the second nucleic acid molecule are unbound to a particle, and wherein the plurality of the second nucleic acid molecule corresponds to an amplified nucleic acid and is in excess relative to the at least one of the first nucleic acid molecule;
wherein each of the at least one of the first nucleic acid molecule comprises an intended base sequence and a base sequence for detection different from the intended base sequence, and wherein the intended base sequence is present in each of the plurality of shapes in a predetermined number that is less than 1,000;
wherein each of the plurality of the second nucleic acid molecule comprises the base sequence for detection and is free of the intended base sequence,
wherein a coefficient of variation (CV value) for the predetermined number in which the intended base sequence is comprised is lower than 20%.

2. The container of claim 1, wherein the at least one of the first nucleic acid molecule comprises the intended base sequence in a plural number in a same molecule.

3. The container of claim 2, wherein when the at least one of the first nucleic acid molecule comprises the intended base sequence in the plural number, the at least one of the first nucleic acid molecule comprises at least one artificial nucleic acid base unamplifiable by a natural nucleic acid synthetase between one intended base sequence and another intended base sequence.

4. The container of claim 1, wherein the at least one of the first nucleic acid molecule and/or the plurality of the second nucleic acid molecule is an artificially synthesized nucleic acid molecule having reduced molecular weight and/or fewer impurities compared to a natural counterpart.

5. The container of claim 1, wherein the container is colored.

6. The container of claim 1, wherein at least the intended base sequence in the at least one of the first nucleic acid molecule is a single-strand nucleic acid.

7. The container of claim 6, wherein the at least one of the first nucleic, acid molecule comprises the base sequence for detection at a 5' terminal side of the intended base sequence.

8. A method for producing a nucleic acid sample-contained container, the method comprising:
forming a plurality of dispersed phases, each of which comprises a nucleic acid that comprises: an intended base sequence; and a base sequence for detection different from the intended base sequence;
amplifying the base sequence for detection in the dispersed phases;
discriminating between positive dispersed phases in which the base sequence for detection has been amplified and negative dispersed phases in which the base sequence for detection has not been amplified among the dispersed phases;
sorting from each other, the positive dispersed phases and the negative dispersed phases discriminated between in the discriminating; and
dispensing a droplet of the positive dispersed phases sorted in the sorting into a container, wherein the container comprises a plurality of shapes selected from the group consisting of a concave bottom and a section on a substrate, wherein the droplet consists of
a solution, wherein the solution is selected from the group consisting of water, nuclease-free water, a broth, a separation liquid, a diluted solution, a buffer, an organic substance lysing liquid, an organic solvent, an electrolyte aqueous solution, an inorganic salt aqueous solution, a metal aqueous solution, a labeling agent or reagent, and a mixture liquid of these solutions;
a nucleic acid amplifying agent and a fluorescent labeling reagent; and
at least one of the intended base sequence and a plurality of the base sequence for detection, wherein the at least one of the intended and the plurality of the base sequence for detection are unbound to a particle, wherein the plurality of the base sequence for detection is in excess relative to the at least one of the intended base sequence,
wherein a number in which the intended base sequence is comprised is less than 1,000, and a coefficient of variation (CV value) for the number in which the intended base sequence is comprised is lower than 20%.

9. The method of claim 8, wherein a probability at which each of the dispersed phases comprises one intended base sequence is 90% or higher.

10. The method of claim 8, wherein the discriminating comprises detecting a light signal emitted by the dispersed phases and discriminating between the positive dispersed phases and the negative dispersed phases.

11. The method of claim 8, wherein the dispensing comprises dispensing the dispersed phases that comprise the nucleic acid that comprises the intended base sequence in a number specified in the discriminating.

12. The method of claim 8, wherein the forming is performed with a nucleic acid-containing liquid that comprises the nucleic acid at a concentration at which the nucleic acid is contained in at most one molecule in each one of the dispersed phases.

13. The method of claim 8, wherein the dispensing is performed by an inkjet method.

14. The method of claim 8, wherein the dispensing is performed with previous counting, before the dispensing, of a number in which the dispersed phases discriminated are present.

15. A nucleic acid sample, consisting of:
a solution, wherein the solution is selected from the group consisting of water, nuclease-free water, a broth, a separation liquid, a diluted solution, a buffer, an organic substance lysing liquid, an organic solvent, an electrolyte aqueous solution, an inorganic salt aqueous solution, a metal aqueous solution, a labeling agent or reagent, and a mixture liquid of these solutions;

a first nucleic acid molecule that comprises a base sequence for detection and a base sequence different from the base sequence for detection; and
a second nucleic acid molecule that comprises the base sequence for detection;
wherein the first nucleic acid molecule and the second nucleic acid molecule are unbound to a particle, and wherein the second nucleic acid molecule corresponds to an amplified nucleic acid and is in excess relative to the at least one of the first nucleic acid molecule
wherein the nucleic acid sample comprises the first nucleic acid molecule in a predetermined number and a plurality of the second nucleic acid molecule, and
wherein a number in which the intended base sequence is comprised is less than 1,000, and a coefficient of variation (CV value) for the number in which the intended base sequence is comprised is lower than 20%.

\* \* \* \* \*

SEQUENCE LISTING

```
<160> NUMBER OF SEQ ID NOS: 13

<210> SEQ ID NO 1
<211> LENGTH: 600
<212> TYPE: DNA
<213> ORGANISM: Artificial Sequence
<220> FEATURE:
<223> OTHER INFORMATION: Synthetic DNA

<400> SEQUENCE: 1
attcgaaggg tgattggatc ggagatagga tgggtcaatc gtagggacaa tcgaagccag      60
aatgcaaggg tcaatggtac gcagaatgga tggcacttag ctagccagtt aggatccgac     120
tatccaagcg tgtatcgtac ggtgtatgct tcggagtaac gatcgcacta agcatggctc     180
aatcctaggc tgataggttc gcacatagca tgccacatac gatccgtgat tgctagcgtg     240
attcgtaccg agaactcacg ccttatgact gcccttatgt caccgcttat gtctcccgag     300
atcacacccg ttatctcagc cctaatctct gcggtttagt ctggccttaa tccatgcctc     360
atagctaccc tcataccatc gctcatacct tccgacattg catccgtcat tccaaccctg     420
attcctacgg tctaacctag cctctatcct acccagttag gttgcctctt agcatccctg     480
ttacgtacgc tcttaccatg cgtcttacct tggcactatc gatgggagta tggtagcgag     540
tatggaacgg actaacgtag gcagtaagct agggtgtaag gttgggacta aggatgccag     600

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
gtcaccgctt atgtctcccg                                                  20

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
gagggtagct atgaggcatg g                                                21

<210> SEQ ID NO 4
<211> LENGTH: 16
```

```
<212> TYPE: DNA
<213> ORGANISM: Artificial Sequence
<220> FEATURE:
<223> OTHER INFORMATION: Synthetic DNA

<400> SEQUENCE: 4
tctcagccct aatctc                                                      16

<210> SEQ ID NO 5
<211> LENGTH: 533
<212> TYPE: RNA
<213> ORGANISM: Artificial Sequence
<220> FEATURE:
<223> OTHER INFORMATION: Synthetic RNA

<400> SEQUENCE: 5
gggcucgacu aguuaauacg guacaggaua accgaucggc uugcaacaua acggcguuaa       60
gaaugcggga gugcaguuuc cgauucucac aucaaucgcc aauaaggccu ugucgcaaua      120
uagacucaac gguucuagua gcugaucggu auuacgugac gcaaccgauu agacaugcac      180
aauuccuugg ucgcuauacu acggaaaucg ucagguacua uaacccgucg caggccuaau      240
acgugucguc acaucgccaa ccuaucguca gucggaaaga cguugcuguc uaccaucgaa      300
acuauuuacc gcuccgagau ucacgaguac gaacucacga ggaaguugcc cuauguaagg      360
uaucacucca gguacugcgc cgauaguacc aggugaucaa acgguugcaa gaaggccacg      420
acguaucggg cucuuuagac guacgcucga gauuaaacgc gcacugauuc acuuuagccc      480
ggaaugucuc ggugcgaugu agaaaaaaaa aaaaaaaaa aaaaaaaaaa aaa             533

<210> SEQ ID NO 6
<211> LENGTH: 136
<212> TYPE: DNA
<213> ORGANISM: Artificial Sequence
<220> FEATURE:
<223> OTHER INFORMATION: Synthetic DNA

<400> SEQUENCE: 6
gtgaatcagt gcgcgtttaa tctcgagcgt acgtctaaag agcccgatac gtcgtggcct       60
tcttgcaacc gtttgatcac ctggtactat cggcgcagta cctggagtga taccttacat      120
agggcaactt cctcgt                                                     136

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA

<400> SEQUENCE: 7
acgaggaagt tgccctatgt aag                                              23

<210> SEQ ID NO 8
<211> LENGTH: 23
<212> TYPE: DNA
<213> ORGANISM: Artificial Sequence
<220> FEATURE:
<223> OTHER INFORMATION: Synthetic DNA

<400> SEQUENCE: 8
gtgaatcagt gcgcgtttaa tct                                              23

<210> SEQ ID NO 9
```

```
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
cggttgcaag aaggccacga cgtatcgggc                                    30

<210> SEQ ID NO 10
<211> LENGTH: 486
<212> TYPE: DNA
<213> ORGANISM: Artificial Sequence
<220> FEATURE:
<223> OTHER INFORMATION: Synthetic DNA

<400> SEQUENCE: 10
cacctaatgt gagagttcac cgaggcaaat gatctgtcaa ccggtgtgat caggacatac   60
gcttaatgcc gtagaagccc gtaagctctc cgcccttaa gaggttgtag acggcagttc   120
taaggaattc aagaggtacg agtggacgcg taagcgaatg acctagacct cggcgttaat   180
taggaccctc taatcgcaaa ctcgactctc gtcccaatcc aatggatgtc cagtgctcgg   240
tagcatgatc gtatgatgcg tatcgctgcg agatatcacg aggaagttgc cctatgtaag   300
gtaacggttg caagaaggcc acgacgtatc gggctcttgc tcgagattaa acgcgcactg   360
attcacgcta gcccaatcct ttgacatctg ctccgaagca aagtcagagc gctgcaatgc   420
aaaacggaac gagtgggggc agcagcgcga gcaccgccgc gccggtgtcc ggacccaaag   480
ctgatc                                                              486

<210> SEQ ID NO 11
<211> LENGTH: 23
<212> TYPE: DNA
<213> ORGANISM: Artificial Sequence
<220> FEATURE:
<223> OTHER INFORMATION: Synthetic DNA

<400> SEQUENCE: 11
cacctaatgt gagagttcac cga                                           23

<210> SEQ ID NO 12
<211> LENGTH: 23
<212> TYPE: DNA
<213> ORGANISM: Artificial Sequence
<220> FEATURE:
<223> OTHER INFORMATION: Synthetic DNA

<400> SEQUENCE: 12
cttagaactg ccgtctacaa cct                                           23

<210> SEQ ID NO 13
<211> LENGTH: 29
<212> TYPE: DNA
<213> ORGANISM: Artificial Sequence
<220> FEATURE:
<223> OTHER INFORMATION: Synthetic DNA

<400> SEQUENCE: 13
tgccgtagaa gcccgtaagc tctccgccc                                     29
```